US012752116B2

(12) United States Patent
Moore et al.

(10) Patent No.: US 12,752,116 B2
(45) Date of Patent: Oct. 6, 2026

(54) AUTOMATED SELECTION OF ELECTRODES AND STIMULATION PARAMETERS IN A DEEP BRAIN STIMULATION SYSTEM EMPLOYING DIRECTIONAL LEADS

(71) Applicant: Boston Scientific Neuromodulation Corporation, Valencia, CA (US)

(72) Inventors: Lisa Moore, Glendale, CA (US); Richard Mustakos, Simi Valley, CA (US); Leon Juarez Paz, Berlin (DE)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 804 days.

(21) Appl. No.: 17/649,504

(22) Filed: Jan. 31, 2022

(65) Prior Publication Data

US 2022/0257950 A1 Aug. 18, 2022

Related U.S. Application Data

(60) Provisional application No. 63/149,167, filed on Feb. 12, 2021.

(51) Int. Cl.
*A61N 1/36* (2006.01)

(52) U.S. Cl.
CPC ..... *A61N 1/36132* (2013.01); *A61N 1/36139* (2013.01); *A61N 1/36192* (2013.01)

(58) Field of Classification Search
CPC ............ A61N 1/36132; A61N 1/36139; A61N 1/36192; A61N 1/37241; A61N 1/37252;
(Continued)

(56) References Cited

U.S. PATENT DOCUMENTS 6,181,969 B1 1/2001 Gord
8,359,100 B2 1/2013 Cameron et al.
(Continued)

FOREIGN PATENT DOCUMENTS

WO 2014/036075 A1 3/2014

OTHER PUBLICATIONS

K. Hoang. et al., “Biomarkers and Stimulation Algorithms for Adaptive Brain Stimulation,” Front. Neurosci., Oct. 9, 2017 Sec. Neuroprosthetics, vol. 11—2017 (Year: 2017).*
(Continued)

*Primary Examiner* — Lynsey C Eiseman
*Assistant Examiner* — Christopher J. Mutchler
(74) *Attorney, Agent, or Firm* — Lewis & Reese, PLLC

(57) ABSTRACT

A programming algorithm is disclosed to efficiently select stimulation parameters for a patient having a Deep Brain Stimulation (DBS) implant, which is especially useful in optimizing stimulation when the DBS implant includes a directional lead capable of providing simulation at a rotational angle θ. The algorithm preferably first simultaneously determines an optimal longitudinal position (Lopt) and amplitude (Iopt1) for stimulation along the lead. This occurs by the algorithm efficiently selecting various values for L and I at which stimulation can be tried on the patient and scored. Once Lopt is determined, and if rotational optimization is possible at this longitudinal position, the algorithm simultaneously determines an optimal rotational angle (θopt) and amplitude (Iopt2) for stimulation around the lead at the optimized longitudinal position Lopt. This also occurs by the algorithm efficiently selecting various values for θ and I at which stimulation can be tried on the patient and scored.

16 Claims, 20 Drawing Sheets

82

(58) Field of Classification Search
CPC . A61N 1/37247; A61N 1/0534; A61N 1/0551
See application file for complete search history.

(56) References Cited

U.S. PATENT DOCUMENTS

| | | | |
|---|---|---|---|
| 8,606,362 | B2 | 12/2013 | He et al. |
| 8,620,436 | B2 | 12/2013 | Parramon et al. |
| 8,702,629 | B2 | 4/2014 | Giuffrida et al. |
| 8,849,408 | B1 | 9/2014 | Gilson et al. |
| 9,211,417 | B2 | 12/2015 | Heldman et al. |
| 9,238,142 | B2 | 1/2016 | Heldman et al. |
| 9,289,603 | B1 | 3/2016 | Giuffrida et al. |
| 9,302,046 | B1 | 4/2016 | Giuffrida et al. |
| 9,364,665 | B2 | 6/2016 | Bokil et al. |
| 9,393,418 | B2 | 7/2016 | Giuffrida et al. |
| 9,522,278 | B1 | 12/2016 | Heldman et al. |
| 9,662,502 | B2 | 5/2017 | Giuffrida et al. |
| 9,717,920 | B1 | 8/2017 | Heldman et al. |
| 9,877,680 | B1 | 1/2018 | Giuffrida et al. |
| 10,092,754 | B1 | 10/2018 | Heldman et al. |
| 10,112,052 | B2 | 10/2018 | Bokil et al. |
| 10,342,970 | B2 | 7/2019 | Goetz et al. |
| 10,478,626 | B1 | 11/2019 | Heldman et al. |
| 10,576,292 | B2 | 3/2020 | Orinski |
| 10,603,498 | B2 | 3/2020 | Blum et al. |
| 2012/0092031 | A1 | 4/2012 | Shi et al. |
| 2012/0095519 | A1 | 4/2012 | Parramon et al. |
| 2012/0095529 | A1 | 4/2012 | Parramon et al. |
| 2015/0080982 | A1 | 3/2015 | Funderburk |
| 2015/0157861 | A1 | 6/2015 | Aghassian |
| 2015/0231402 | A1 | 8/2015 | Aghassian |
| 2015/0360038 | A1 | 12/2015 | Zottola et al. |
| 2017/0259064 | A1 | 9/2017 | Wu et al. |
| 2018/0071520 | A1 | 3/2018 | Weerakoon et al. |
| 2018/0071527 | A1 | 3/2018 | Feldman et al. |
| 2018/0104500 | A1 | 4/2018 | Blum et al. |
| 2018/0140831 | A1 | 5/2018 | Feldman et al. |
| 2019/0030321 | A1 | 1/2019 | Tinkhauser |
| 2019/0076645 | A1 | 3/2019 | Bower et al. |
| 2019/0083796 | A1 | 3/2019 | Weerakoon et al. |
| 2019/0117978 | A1 | 4/2019 | Desai et al. |
| 2019/0126032 | A1 | 5/2019 | Cheeran et al. |
| 2019/0175915 | A1 | 6/2019 | Brill et al. |
| 2019/0184171 | A1 | 6/2019 | Mustakos et al. |
| 2020/0001091 | A1 | 1/2020 | Marnfeldt |
| 2021/0196956 | A1 | 7/2021 | Juarez Paz |

OTHER PUBLICATIONS

Bronstein JM et al., "Deep brain stimulation for Parkinson disease: an expert consensus and review of key issues," Arch Neurol. Feb. 2011;68(2):165. (Year: 2011).*

International Search Report and Written Opinion regarding corresponding PCT Application No. PCT/US2022/070442, mailed May 2, 2022.

* cited by examiner

230

| Step(i) | L | I | Electrode config. (* -I) | S |
|---|---|---|---|---|
| 1 | 1 | 2 | E11=E12=E13=33.3% | 1.2 |
| 2 | 6 | 2 | E2=100% | 3 |
| 3 | 3.5 | 3.5 | E4=50%; E5=E6=E7=16.7% | 0.5 |
| 4 | 5 | 6.0 | E3=100% | 1 |
| 5 | 0 | 0.8 | E14=E15=E16=33.3% | 2 |
| 6 | 6.5 | 3.7 | E1=E2=50% | 2.9 |
| ***7*** | ***1.5*** | ***5.0*** | E8 through E13=16.7% | ***0.4*** |
| 8 | 3.2 | 1.2 | E4=20%; E5=E6=E7=26.3% | 1 |
| 9 | 2.2 | 2.3 | E5=E6=E7=6.7%; E8=E9=E10=26.7% | 3 |

presets (steps 1–3)

⋮

(Lopt,Iopt1) = (1.5, 5.0)

*A: Inverse Distance*

$$R_A(L,I) = \frac{\sum_{j=1}^{n}\left(\frac{S_j}{(d_j)^p}\right)}{\sum_{j=1}^{n}\left(\frac{1}{(d_j)^p}\right)}$$

where:

- n = number of previously tested points
- S = score at those previous tested points
- d = distance to each previously tested point
- p = power parameter

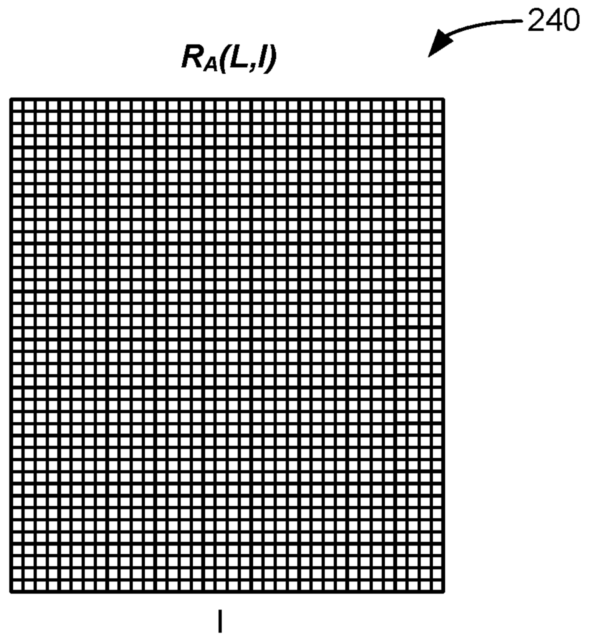

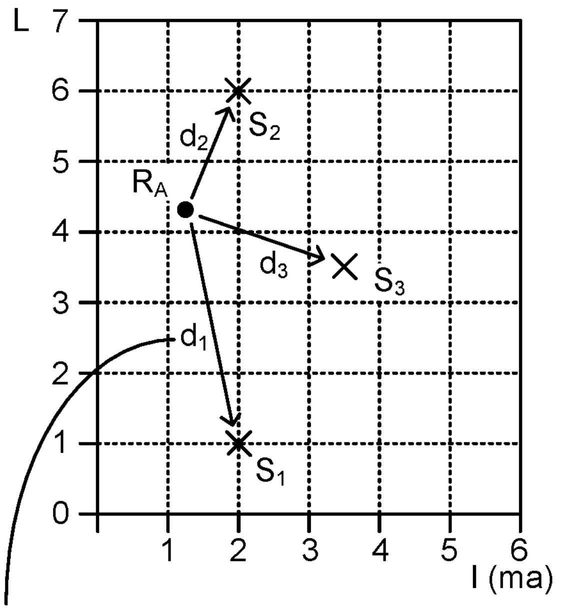

$$d_1 = \sqrt{(I_A - I_1)^2 + (L_A - L_1)^2}$$

$R_A(L,I)$ comprises an estimated or predicted score based on scores at previously tested points and distance to those points

*Figure 9A*

*B: Absolute Distance*

$$R_B(L,I) = -\sum_{j=1}^{n} d_j$$

where:

n = number of previously tested points
d = distance to each previously tested point $R_B(L,I)$ favors selecting next (L,I) at points furthest from previously tested points

*C: Distance Variance*

$$R_C(L,I) = Var(d) = \sqrt{\sum_{j=1}^{n} (d_j - d(avg))^2)/(n-1)}$$

where:
n = number of previously tested points
d = distance to each previously tested point $R_C(L,I)$ favors selecting next (L,I) at points with little variance in distance to previously tested points

*Determine an optimized rotational angle (θopt) and amplitude (Iopt2) for stimulation at Lopt (400):*
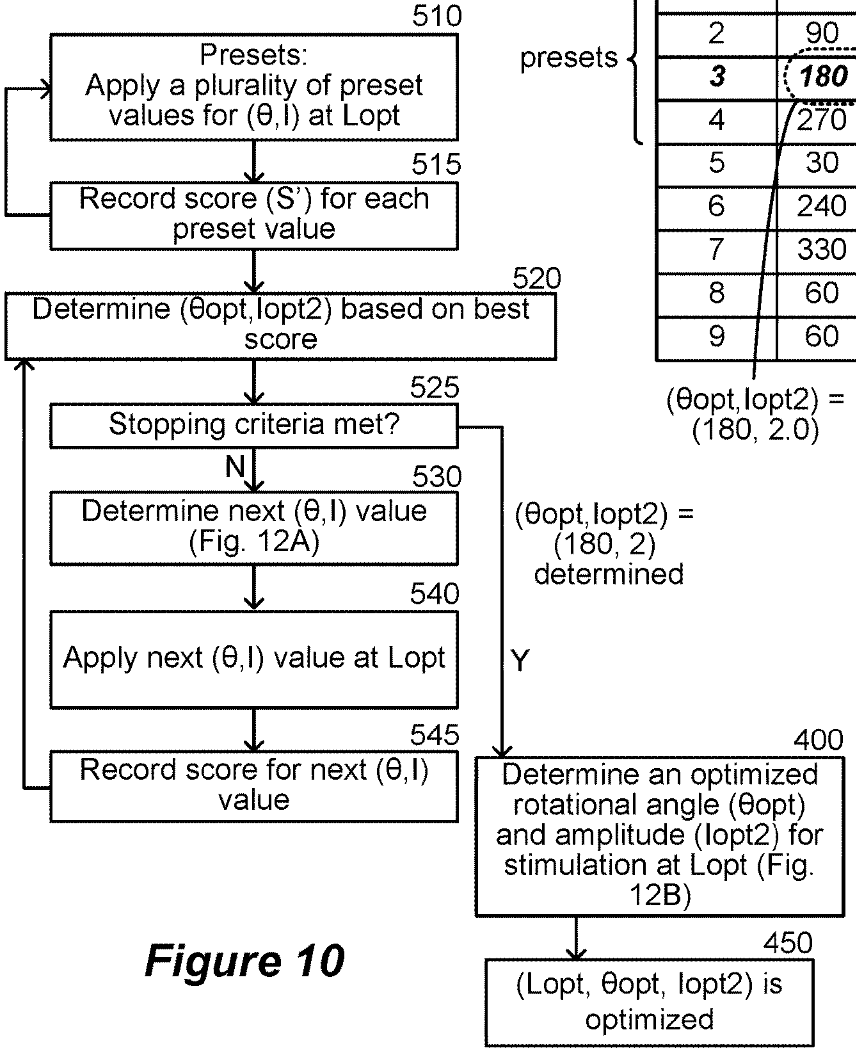
Figure 10
230'
| ***Step(i)*** | ***θ*** | ***I*** | ***Electrode config. (* -I)*** | ***S'*** |
|---|---|---|---|---|
| 1 | 0 | 2 | E9=E12=50% | 3 |
| 2 | 90 | 3.5 | E9=E12=12.5%, E10=E13=37.5% | 2 |
| ***3*** | ***180*** | ***2*** | E8=E10=E11=E13=25% | ***0.3*** |
| 4 | 270 | 3.5 | E9=E12=12.5%, E8=E11=37.5% | 1 |
| 5 | 30 | 4.5 | E9=E12=37.5%, E10=E13=12.5% | 2 |
| 6 | 240 | 2.7 | E8=E11=50% | 3.1 |
| 7 | 330 | 3.2 | E9=E12=37.5%, E8=E11=12.5% | 2 |
| 8 | 60 | 1.5 | E9=E12=E10=E13=25% | 1 |
| 9 | 60 | 3.8 | E9=E12=E10=E13=25% | 1.5 |
presets (steps 1–4)
(θopt,Iopt2) = (180, 2.0)
⋮
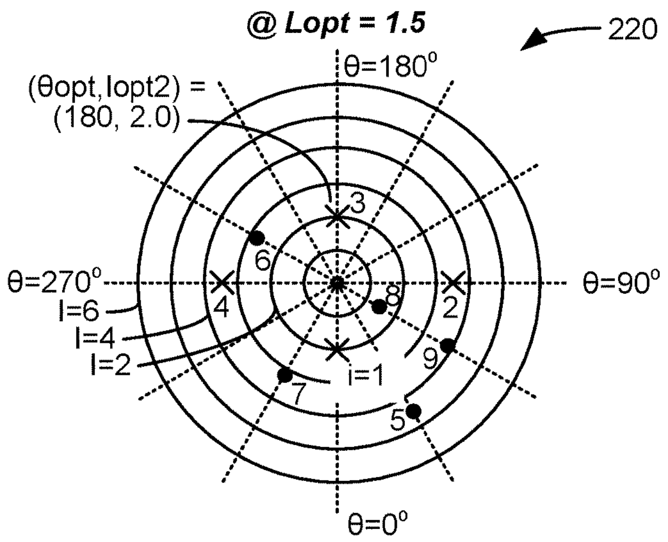

| $\theta_1$ | $I_1$ |
|---|---|
| 60° | 3.8 |

→

| $X_1$ | $Y_1$ | $I_1$ |
|---|---|---|
| 6 | 2√3 | 3.8 |

| $\theta_2$ | $I_2$ |
|---|---|
| 330° | 6.0 |

→

| $X_2$ | $Y_2$ | $I_2$ |
|---|---|---|
| 3 | √3 | 6.0 |

Calculating distance d' from point $(\theta_1, I_1)$ to $(\theta_2, I_2)$:

$$d' = \sqrt{a\,(I_2 - I_1)^2 + b\,(X_2 - X_1)^2 + b\,(Y_2 - Y_1)^2}$$

*A: Inverse Distance*

$$R'_A(\theta, I) = \frac{\sum_{j=1}^{n}\left(\frac{S'_j}{(d'_j)^{p}}\right)}{\sum_{j=1}^{n}\left(\frac{1}{(d'_j)^{p}}\right)}$$

*B: Absolute Distance*

$$R'_B(\theta, I) = -\sum_{j=1}^{n} d'_j$$

*C: Distance Variance*

$$R'_C(\theta, I) = Var(d') = \sqrt{\sum_{j=1}^{n} (d'_j - d'(avg))^2)/(n-1)}$$

*D: Lower Amplitude Preference*

Set values not based on previously tested points

Longitudinal optimization:

| Step(i) | L | I | S |
|---|---|---|---|
| 1 | 1 | 2 | 1.2 |
| 2 | 6 | 2 | 3 |
| 3 | 3.5 | 3.5 | 0.5 |
| 4 | 5 | 6.0 | -- |

| Lopt | Iopt1 | S | Electrode config. (*-I) |
|---|---|---|---|
| 1.5 | 5.0 | 0.4 | E8 through E13=16.7% |

Rotational optimization (at Lopt):

| Step(i) | θ | I | S' |
|---|---|---|---|
| 1 | 0 | 2 | 3 |
| 2 | 90 | 3.5 | 2 |
| 3 | 180 | 2 | 0.7 |
| 4 | 270 | 3.5 | 1 |
| 5 | 30 | 4.5 | -- |

| Lopt | θopt | Iopt2 | S' | Electrode config. (*-I) |
|---|---|---|---|---|
| 1.5 | 180 | 2 | 0.7 | E8=E10=E11=E13=25% |

82

230

| Step(i) | L | I | Electrode config. (* -I) | $S_1$ | $S_2$ | $S_3$ | $S_T$ |
|---|---|---|---|---|---|---|---|
| 1 | 1 | 2 | E11=E12=E13=33.3% | 1.2 | 2 | 1 | 1.4 |
| 2 | 6 | 2 | E2=100% | 3 | 2 | 2 | 2.3 |
| 3 | 3.5 | 3.5 | E4=50%; E5=E6=E7=16.7% | 0.5 | 0 | 1 | 0.5 |
| 4 | 5 | 6.0 | E3=100% | 1 | 1.5 | 2 | 1.5 |
| 5 | 0 | 0.8 | E14=E15=E16=33.3% | 2 | 2 | 2 | 2 |
| 6 | 6.5 | 3.7 | E1=E2=50% | 2.9 | 3 | 2 | 2.7 |
| 7 | 1.5 | 5.0 | E8 through E13=16.7% | ***0.4*** | 1 | 1.5 | 1.0 |
| 8 | 3.2 | 1.2 | E4=20%; E5=E6=E7=26.3% | 1 | 0 | 0 | ***0.3*** |
| 9 | 2.2 | 2.3 | E5=E6=E7=6.7%; E8=E9=E10=26.7% | 3 | 2 | 2.5 | 2.5 |

presets (steps 1–3)

⋮

*Example 1:* $S_T = e{*}S_1+f{*}S_2+g{*}S_3 \longrightarrow R_{TA}(L,I),\ R_{TB}(L,I),\ R_{TC}(L,I),\ R_{TD}(L,I) \xrightarrow{w_{TA},\ w_{TB},\ w_{TC},\ w_{TD}} R_W(L,I) \longrightarrow$ Next (L,I) value

*Example 2:*

$S_1 \longrightarrow R_{1A}(L,I),\ R_{1B}(L,I),\ R_{1C}(L,I),\ R_{1D}(L,I) \xrightarrow{w_{1A},\ w_{1B},\ w_{1C},\ w_{1D}} R_{1W}(L,I)$ $S_2 \longrightarrow R_{2A}(L,I),\ R_{2B}(L,I),\ R_{2C}(L,I),\ R_{2D}(L,I) \xrightarrow{w_{2A},\ w_{2B},\ w_{2C},\ w_{2D}} R_{2W}(L,I)$ $S_3 \longrightarrow R_{3A}(L,I),\ R_{3B}(L,I),\ R_{3C}(L,I),\ R_{3D}(L,I) \xrightarrow{w_{3A},\ w_{3B},\ w_{3C},\ w_{3D}} R_{3W}(L,I)$ $R_W(L,I) = e{*}R_{1W}(L,I)+f{*}R_{2W}(L,I)+g{*}R_{3W}(L,I)$ $\downarrow$ Next (L,I) value

*Figure 14*

AUTOMATED SELECTION OF ELECTRODES AND STIMULATION PARAMETERS IN A DEEP BRAIN STIMULATION SYSTEM EMPLOYING DIRECTIONAL LEADS

CROSS-REFERENCE TO RELATED APPLICATIONS

This application is a non-provisional application based on U.S. Provisional Patent Application Ser. No. 63/149,167, filed Feb. 12, 2021, which is incorporated herein by reference, and to which priority is claimed.

FIELD OF THE INVENTION

This application relates to Implantable Stimulator Devices (ISD), and more specifically to an algorithm for selecting electrodes and stimulation parameters in an ISD such as a Deep Brain Stimulation (DBS) device.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Deep Brain Stimulation (DBS) system, such as that disclosed in U.S. Patent Application Publication 2020/0001091, which is incorporated herein by reference. However, the present invention may find applicability with any implantable neurostimulator device system, including Spinal Cord Stimulation (SCS) systems, Vagus Nerve Stimulation (VNS) system, Sacral Nerve Stimulation (SNS) systems, and the like.

A DBS system typically includes an Implantable Pulse Generator (IPG) 10 shown in FIG. 1A. The IPG 10 includes a biocompatible device case 12 that holds the circuitry and a battery 14 for providing power for the IPG to function, although the IPG 10 can also lack a battery and can be wirelessly powered by an external source. The IPG 10 is coupled to tissue-stimulating electrodes 16 via one or more electrode leads 18 or 19, which are shown in more details in FIGS. 1B and 1C.

FIG. 1B shows a lead 18 having eight ring-shaped electrodes 16 which are located at different longitudinal positions along a central axis 15. Lead 18 is referred to herein as a "non-directional lead," because the ring-shaped electrodes span 360 degrees around the axis 15, and thus cannot direct stimulation to different rotational positions around the axis 15.

FIG. 1C shows a lead 19 also having eight electrodes, but not all of the electrodes are ring-shaped. Electrode E8 at the distal end of the lead 19 and electrode E1 at a proximal end of the lead are ring-shaped. Electrodes E2, E3, and E4, by contrast, comprise split-ring electrodes, each of which are located at the same longitudinal position along the axis 15, but each spanning less than 360 degrees around the axis. For example, each of electrodes E2, E3, and E4 may span 90 degrees around the axis 15, with each being separated from the others by gaps of 30 degrees. Electrodes E5, E6, and E7 also comprise split-ring electrodes, but are located at a different longitudinal position. Lead 19 is referred to herein as a "directional lead," because at least some of the electrodes at a given longitudinal position (e.g., E2, E3, E4) span less than 360 degrees, meaning that those electrodes can direct stimulation to different rotational positions around the axis 15. In other designs of a directional lead 19, all electrodes can be split-ring, or there could be different numbers of split-ring electrodes at each longitudinal position (i.e., more or less than three).

Lead wires 20 within the leads are coupled to the electrodes 16 and to proximal contacts 21 insertable into lead connectors 22 fixed in a header 23 on the IPG 10, which header can comprise an epoxy for example. Alternatively, the proximal contacts 21 may connect to lead extensions (not shown) which are in turn inserted into the lead connectors 22. Once inserted, the proximal contacts 21 connect to header contacts 24 within the lead connectors 22, which are in turn coupled by feedthrough pins 25 through a case feedthrough 26 to stimulation circuitry 28 within the case 12, which stimulation circuitry 28 is described below.

In the IPG 10 illustrated in FIG. 1A, there are thirty-two electrodes (E1-E32), split between four percutaneous leads 18 or 19 (18 is shown), and thus the header 23 may include a 2×2 array of eight-electrode lead connectors 22. However, the type and number of leads, and the number of electrodes, in an IPG is application specific and therefore can vary. In another example not shown, a given lead can have 16 sixteen electrodes, and thus this lead would have two sets of proximal contacts 21 to mate with two of the eight-electrode lead connectors 22, as disclosed for example in U.S. Patent Application Publication 2019/0076645. The conductive case 12 can also comprise an electrode (Ec).

In a DBS application, as is useful in the treatment of tremor in Parkinson's disease for example, the IPG 10 is typically implanted under the patient's clavicle (collarbone). Leads 18 or 19 (perhaps as extended by lead extensions, not shown) are tunneled through and under the neck and the scalp, with the electrodes 16 implanted through holes drilled in the skull and positioned for example in the subthalamic nucleus (STN) and the pedunculopontine nucleus (PPN) in each brain hemisphere. The IPG 10 can also be implanted underneath the scalp closer to the location of the electrodes' implantation, as disclosed for example in U.S. Pat. No. 10,576,292. The IPG lead(s) 18 or 19 can be integrated with and permanently connected to the IPG 10 in other solutions.

IPG 10 can include an antenna 27*a* allowing it to communicate bi-directionally with a number of external devices discussed subsequently. Antenna 27*a* as shown comprises a conductive coil within the case 12, although the coil antenna 27*a* can also appear in the header 23. When antenna 27*a* is configured as a coil, communication with external devices preferably occurs using near-field magnetic induction. IPG 10 may also include a Radio-Frequency (RF) antenna 27*b*. In FIG. 1A, RF antenna 27*b* is shown within the header 23, but it may also be within the case 12. RF antenna 27*b* may comprise a patch, slot, or wire, and may operate as a monopole or dipole. RF antenna 27*b* preferably communicates using far-field electromagnetic waves, and may operate in accordance with any number of known RF communication standards, such as Bluetooth, Zigbee, WiFi, MICS, and the like. If the IPG 10 lacks a battery 14, an additional coil can be present to receive wireless power from an external source.

Stimulation in IPG 10 is typically provided by pulses each of which may include a number of phases such as 30*a* and 30*b*, as shown in the example of FIG. 2A. In the example shown, such stimulation is monopolar, meaning that a current is provided between at least one selected lead-based electrode (e.g., E1) and the case electrode Ec 12. Stimulation parameters typically include amplitude (current I, although a voltage amplitude V can also be used); frequency (F); pulse width (PW) of the pulses or of its individual phases such as 30*a* and 30*b*; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E1 has been selected as a cathode (during its first phase 30*a*), and thus provides pulses which sink a negative current of amplitude –I from the tissue. The case electrode Ec has been selected as an anode (again during first phase 30*a*), and thus provides pulses which source a corresponding positive current of amplitude +I to the tissue. Note that at any time the current sunk from the tissue (e.g., –I at E1 during phase 30*a*) equals the current sourced to the tissue (e.g., +I at Ec during phase 30*a*). The polarity of the currents at these electrodes can be changed: for example, during first phase 30*a*, Ec can be selected as a cathode, and E1 can be selected as an anode, etc.

IPG 10 as mentioned includes stimulation circuitry 28 to form prescribed stimulation at a patient's tissue. FIG. 3 shows an example of stimulation circuitry 28, which includes one or more current sources $40_i$ and one or more current sinks 42*k*. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node ei 39. Each electrode node ei 39 is connected to an electrode Ei 16 via a DC-blocking capacitor Ci 38, for the reasons explained below. PDACs $40_i$ and NDACs $42_i$ can also comprise voltage sources.

Proper control of the PDACs $40_i$ and NDACs $42_i$ allows any of the electrodes 16 and the case electrode Ec 12 to act as anodes or cathodes to create a current through a patient's tissue, Z, hopefully with good therapeutic effect. In the example shown, and consistent with the first pulse phase 30*a* of FIG. 2A, electrode E1 has been selected as a cathode electrode to sink current from the tissue Z and case electrode Ec has been selected as an anode electrode to source current to the tissue Z. Thus PDAC 40*c* and NDAC 421 are activated and digitally programmed to produce the desired current, I, with the correct timing (e.g., in accordance with the prescribed frequency F and pulse width PW). Power for the stimulation circuitry 28 is provided by a compliance voltage VH, as described in further detail in U.S. Patent Application Publication 2013/0289665. Other stimulation circuitries 28 can also be used in the IPG 10. In an example not shown, a switching matrix can intervene between the one or more PDACs $40_i$ and the electrode nodes ei 39, and between the one or more NDACs $42_i$ and the electrode nodes. Switching matrices allows one or more of the PDACs or one or more of the NDACs to be connected to one or more electrode nodes at a given time. Various examples of stimulation circuitries can be found in U.S. Pat. Nos. 6,181,969, 8,606,362, 8,620,436, U.S. Patent Application Publications 2018/0071520 and 2019/0083796.

Much of the stimulation circuitry 28 of FIG. 3, including the PDACs $40_i$ and NDACs $42_i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as telemetry circuitry (for interfacing off chip with telemetry antennas 27*a* and/or 27*b*), circuitry for generating the compliance voltage VH, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

Referring again to FIG. 2A, the stimulation pulses as shown are biphasic, with each pulse comprising a first phase 30*a* followed thereafter by a second phase 30*b* of opposite polarity. Biphasic pulses are useful to actively recover any charge that might be stored on capacitive elements in the electrode current paths, such as on the DC-blocking capacitors 38, as is well known. FIG. 3 also shows that stimulation circuitry 28 can include passive recovery switches $41_i$, which are described further in U.S. Patent Application Publications 2018/0071527 and 2018/0140831. Passive recovery switches $41_i$ may be closed to passively recover any charge remaining on the DC-blocking capacitors Ci 38 after issuance of the second pulse phase 30*b*—i.e., to recover charge without actively driving a current using the DAC circuitry, as shown during duration 30*c*. Alternatively, passive charge recovery can be used during the second pulse phase 30*b* after the actively driven first pulse phase 30*a*, although this isn't shown in FIG. 2A. Again, passive charge recovery is well known and not further described.

FIG. 4 shows the communication environment of the IPG 10, which includes external devices that can wirelessly communicate data with the IPG 10, including a patient, hand-held external controller 60, and a clinician programmer 70. Both of devices 60 and 70 can be used to wirelessly transmit a stimulation program to the IPG 10—that is, to program their stimulation circuitries to produce stimulation with a desired amplitude and timing described earlier. Both devices 60 and 70 may also be used to adjust one or more stimulation parameters of a stimulation program that the IPG 10 is currently executing. Devices 60 and 70 may also wirelessly receive information from the IPG 10, such as various status information, etc.

External controller 60 can be as described in U.S. Patent Application Publication 2015/0080982 for example, and may comprise a controller dedicated to work with the IPG 10. External controller 60 may also comprise a general-purpose mobile electronics device such as a mobile phone which has been programmed with a Medical Device Application (MDA) allowing it to work as a wireless controller for the IPG 10, as described in U.S. Patent Application Publication 2015/0231402. External controller 60 includes a user interface, preferably including means for entering commands (e.g., buttons or selectable graphical elements) and a display 62. The external controller 60's user interface enables a patient to adjust stimulation parameters, although it may have limited functionality when compared to the more-powerful clinician programmer 70, described shortly. The external controller 60 can have one or more antennas capable of communicating with the IPG 10. For example, the external controller 60 can have a near-field magnetic-induction coil antenna 64*a* capable of wirelessly communicating with the coil antenna 27*a* or 56*a* in the IPG 10. The external controller 60 can also have a far-field RF antenna 64*b* capable of wirelessly communicating with the RF antenna 27*b* or 56*b* in the IPG 10.

Clinician programmer 70 is described further in U.S. Patent Application Publication 2015/0360038, and can comprise a computing device 72, such as a desktop, laptop, or notebook computer, a tablet, a mobile smart phone, a Personal Data Assistant (PDA)-type mobile computing device, etc. In FIG. 4, computing device 72 is shown as a laptop computer that includes typical computer user interface means such as a screen 74, a mouse, a keyboard, speakers, a stylus, a printer, etc., not all of which are shown for convenience. Also shown in FIG. 4 are accessory devices for the clinician programmer 70 that are usually specific to its operation as a stimulation controller, such as a communication "wand" 76 couplable to suitable ports on the computing device 72, such as USB ports 79 for example. The antenna used in the clinician programmer 70 to communicate with the IPG 10 can depend on the type of antennas included in those devices. If the patient's IPG 10 includes a coil antenna 27*a*, wand 76 can likewise include a coil antenna 80*a* to establish near-field magnetic-induction communications at small distances. In this instance, the wand 76 may be affixed in close proximity to the patient, such as by placing the wand 76 in a belt or holster wearable by the patient and proximate to the patient's IPG 10. If the IPG 10 includes an RF antenna 27*b*, the wand 76, the computing device 72, or both, can likewise include an RF antenna 80*b* to establish communication at larger distances. The clinician programmer 70 may also communicate with other devices and networks, such as the Internet, either wirelessly or via a wired link provided at an Ethernet or network port.

To program stimulation programs or parameters for the IPG 10, the clinician interfaces with a clinician programmer graphical user interface (GUI) 82 provided on the display 74 of the computing device 72. As one skilled in the art understands, the GUI 82 can be rendered by execution of clinician programmer software 84 stored in the computing device 72, which software may be stored in the device's non-volatile memory 86. Clinician programmer software 84 may also reside in network 50 or server 51, as described further below. Execution of the clinician programmer software 84 in the computing device 72 can be facilitated by control circuitry 88 such as one or more microprocessors, microcomputers, FPGAs, DSPs, other digital logic structures, etc., which are capable of executing programs in a computing device, and which may comprise their own memories. For example, control circuitry 88 can comprise an i5 processor manufactured by Intel Corp, as described at https://www.intel.com/content/www/us/en/products/processors/core/i5-processors.html. Such control circuitry 88, in addition to executing the clinician programmer software 84 and rendering the GUI 82, can also enable communications via antennas 80*a* or 80*b* to communicate stimulation parameters chosen through the GUI 82 to the patient's IPG 10.

The IPG 10, external controller 60, and clinician programmer 70, as well as communicating with each other, can communicate with a network 50. Network 50 can comprise a WiFi gateway and the Internet for example, and communication between the devices can occur using the network as an intermediary. A server 51 can be connected to the network, which can for example be used to send stimulation programs or other useful information (e.g., software updates) to the various devices.

SUMMARY

A method is disclosed for optimizing stimulation for a patient having an implantable stimulator device, wherein the stimulation device comprises a lead with a plurality of electrodes for providing stimulation in accordance with stimulation parameters. The method may comprise: determining for the patient through testing an optimized longitudinal position along an axis of the lead and a first optimized amplitude for stimulation, wherein the optimized longitudinal position and the first optimized amplitude comprise first stimulation parameters; determining whether the optimized longitudinal position is proximate to a set of directional electrodes on the lead, wherein the set of directional electrodes span around the axis of the lead at different rotational positions; if the optimized longitudinal position is not proximate to the set of directional electrodes on the lead, determining that the first stimulation parameters are optimized for the patient; and if the optimized longitudinal position is proximate to the set of directional electrodes on the lead, determining for the patient through testing an optimized rotational position and a second optimized amplitude for stimulation at the optimized longitudinal position, wherein the optimized longitudinal position, the optimized rotational position, and the second optimized amplitude comprise second stimulation parameters, and wherein the second stimulation parameters are determined to be optimized for the patient.

In one example, determining the optimized longitudinal position and the first optimized amplitude comprises: providing stimulation at a plurality of different first combinations of longitudinal positions and amplitudes along the lead, and receiving at least one first score at each of the first combinations; and determining the optimized longitudinal position and the first optimized amplitude using at least the at least one first score at each of the first combinations. In one example, at least some of the different first combinations are determined through an iterative process. In one example, the iterative process provides stimulation at initial first combinations, and automatically determines a next first combination for providing stimulation using at least the at least one first score at each of the initial first combinations. In one example, the method further comprises determining at least one first factor. In one example, the at least one first factor is determined at a plurality of possible combinations of longitudinal positions and amplitudes. In one example, the at least one first factor is determined at the plurality of possible combinations of longitudinal positions and amplitudes using a distance between each of the plurality of possible combinations and each of the initial first combinations. In one example, there are a plurality of first factors, and wherein the first factors are used to determine weighted first factors at the possible combinations of longitudinal positions and amplitudes. In one example, the next first combination is determined at a best value of the weighted first factors. In one example, the iterative process repeats to determine subsequent next first combinations using at least the at least one first score at each of the initial first combinations and the at least one first score at the next first combination. In one example, the at least one first score at each of the first combinations is indicative of a patient symptom, a patient response, or a side effect to the provided stimulation.

In one example, determining the optimized rotational position and the second optimized amplitude comprises: providing stimulation at a plurality of different second combinations of rotational positions and amplitudes at the optimized longitudinal position using at least the set of directional electrodes, and receiving at least one second score at each of the second combinations; and determining the optimized rotational position and the second optimized amplitude for the patient using at least the at least one second score at each of the second combinations. In one example, at least some of the different second combinations are determined through an iterative process. In one example, the iterative process provides stimulation at initial second combinations, and automatically determines a next second combination for providing stimulation using at least the at least one second score at each of the initial second combinations. In one example, the method further comprises determining at least one second factor. In one example, the at least one second factor is determined at a plurality of possible combinations of rotational positions and amplitudes. In one example, the at least one second factor is determined at the plurality of possible combinations of rotational and amplitudes using a distance between each of the plurality of possible combinations and each of the initial second combinations. In one example, there are a plurality of second factors, and wherein the second factors are used to determine weighted second factors at the possible combinations of rotational positions and amplitudes. In one example, the next second combination is determined at a best value of the weighted second factors. In one example, the iterative process repeats to determine subsequent next second combinations using at least the at least one second score at each of the initial second combinations and the at least one second score at the next second combination. In one example, the at least one second score at each of the second combinations is indicative of a patient symptom, a patient response, or a side effect to the provided stimulation.

A system is disclosed, comprising: an implantable stimulator device implantable in a patient, wherein the stimulation device comprises a lead with a plurality of electrodes for providing stimulation in accordance with stimulation parameters; and an external device programmed with an algorithm and configured to communicate with the implantable stimulator device, wherein the algorithm is configured to determine for the patient through testing an optimized longitudinal position along an axis of the lead and a first optimized amplitude for stimulation, wherein the optimized longitudinal position and the first optimized amplitude comprise first stimulation parameters; determine whether the optimized longitudinal position is proximate to a set of directional electrodes on the lead, wherein the set of directional electrodes span around the axis of the lead at different rotational positions; if the optimized longitudinal position is not proximate to the set of directional electrodes on the lead, determine that the first stimulation parameters are optimized for the patient; and if the optimized longitudinal position is proximate to the set of directional electrodes on the lead, determine for the patient through testing an optimized rotational position and a second optimized amplitude for stimulation at the optimized longitudinal position, wherein the optimized longitudinal position, the optimized rotational position, and the second optimized amplitude comprise second stimulation parameters, and wherein the second stimulation parameters are determined to be optimized for the patient.

In one example, to determine the optimized longitudinal position and the first optimized amplitude, the algorithm is configured to: provide stimulation at a plurality of different first combinations of longitudinal positions and amplitudes along the lead, and receive at least one first score at each of the first combinations; and determine the optimized longitudinal position and the first optimized amplitude using at least the at least one first score at each of the first combinations. In one example, the algorithm is configured to determine at least some of the different first combinations through an iterative process. In one example, the iterative process provides stimulation at initial first combinations, and automatically determines a next first combination for providing stimulation using at least the at least one first score at each of the initial first combinations. In one example, the algorithm is configured to determine at least one first factor. In one example, the at least one first factor is determined at a plurality of possible combinations of longitudinal positions and amplitudes. In one example, the at least one first factor is determined at the plurality of possible combinations of longitudinal positions and amplitudes using a distance between each of the plurality of possible combinations and each of the initial first combinations. In one example, there are a plurality of first factors, and wherein the first factors are used to determine weighted first factors at the possible combinations of longitudinal positions and amplitudes. In one example, the next first combination is determined at a best value of the weighted first factors. In one example, the iterative process repeats to determine subsequent next first combinations using at least the at least one first score at each of the initial first combinations and the at least one first score at the next first combination. In one example, the at least one first score at each of the first combinations is indicative of a patient symptom, a patient response, or a side effect to the provided stimulation.

In one example, to determine the optimized rotational position and the second optimized amplitude, the algorithm is configured to: provide stimulation at a plurality of different second combinations of rotational positions and amplitudes at the optimized longitudinal position using at least the set of directional electrodes, and receive at least one second score at each of the second combinations; and determine the optimized rotational position and the second optimized amplitude for the patient using at least the at least one second score at each of the second combinations. In one example, the algorithm is configured to determine at least some of the different second combinations through an iterative process. In one example, the iterative process provides stimulation at initial second combinations, and automatically determines a next second combination for providing stimulation using at least the at least one second score at each of the initial second combinations. In one example, the algorithm is configured to determine at least one second factor. In one example, the at least one second factor is determined at a plurality of possible combinations of rotational positions and amplitudes. In one example, the at least one second factor is determined at the plurality of possible combinations of rotational positions and amplitudes using a distance between each of the plurality of possible combinations and each of the initial second combinations. In one example, there are a plurality of second factors, and wherein the second factors are used to determine weighted second factors at the possible combinations of rotational positions and amplitudes. In one example, the next second combination is determined at a best value of the weighted second factors. In one example, the iterative process repeats to determine subsequent next second combinations using at least the at least one second score at each of the initial second combinations and the at least one second score at the next second combination. In one example, the at least one second score at each of the second combinations is indicative of a patient symptom, a patient response, or a side effect to the provided stimulation.

A method is disclosed for optimizing stimulation for a patient having an implantable stimulator device, wherein the stimulation device comprises a lead with a plurality of electrodes for providing stimulation in accordance with stimulation parameters, wherein the lead comprises at least one set of directional electrodes spanning around the axis of the lead at different rotational positions and at a common longitudinal position along the lead. The method may comprise: (a) providing stimulation at a plurality of different combinations of rotational positions and amplitudes using electrodes at least in the set of directional electrodes, and receiving at least one score at each of the combinations; (b) automatically determining a next combination of rotational position and amplitude for providing stimulation using at least the at least one score at each of the combinations; (c) providing stimulation at the next combination using electrodes at least in the set of directional electrodes, and receiving at least one score at the next combination; (d) iteratively repeating steps (b) and (c) to arrive at a data set of combinations of rotational positions and amplitudes and at least one score associated with each combination; and (e) determining an optimized rotational position and an optimized amplitude for the patient using the at least one scores associated with each of the combinations.

In one example, step (b) comprises determining at least one factor at a plurality of possible combinations of rotational positions and amplitudes. In one example, the at least one factor is determined at the plurality of possible combinations of rotational positions and amplitudes using a distance between each of the plurality of possible combinations and each of the initial combinations. In one example, the at least one factor is determined at the plurality of possible combinations of rotational positions and amplitudes using the at least one score at each of the combinations. In one example, there are a plurality of factors, and wherein the factors are used to determine weighted factors at the possible combinations of rotational positions and amplitudes. In one example, the next combination is determined at a best value of the weighted factors. In one example, the at least one score at each of the combinations is indicative of a patient symptom, a patient response, or a side effect to the provided stimulation. In one example, the at least one set of directional electrodes comprise split ring electrodes. In one example, wherein the method further comprises, before step (a), determining an optimized longitudinal position for the stimulation for the patient along the lead. In one example, the optimized longitudinal position is proximate to the set of directional electrodes. In one example, the optimized longitudinal position, the optimized rotational position, and the optimized amplitude comprise optimized stimulation parameters for the patient.

A system is disclosed, comprising: an implantable stimulator device implantable in a patient, wherein the stimulation device comprises a lead with a plurality of electrodes for providing stimulation in accordance with stimulation parameters, wherein the lead comprises at least one set of directional electrodes spanning around the axis of the lead at different rotational positions and at a common longitudinal position along the lead; and an external device programmed with an algorithm and configured to communicate with the implantable stimulator device, wherein the algorithm is configured to (a) provide stimulation at a plurality of different combinations of rotational positions and amplitudes using electrodes at least in the set of directional electrodes, and receiving at least one score at each of the combinations; (b) automatically determine a next combination of rotational position and amplitude for providing stimulation using at least the at least one score at each of the combinations; (c) provide stimulation at the next combination using electrodes at least in the set of directional electrodes, and receiving at least one score at the next combination; (d) iteratively repeat steps (b) and (c) to arrive at a data set of combinations of rotational positions and amplitudes and at least one score associated with each combination; and (e) determine an optimized rotational position and an optimized amplitude for the patient using the at least one scores associated with each of the combinations.

In one example, the algorithm is configured at step (b) to determine at least one factor at a plurality of possible combinations of rotational positions and amplitudes. In one example, the at least one factor is determined at the plurality of possible combinations of rotational positions and amplitudes using a distance between each of the plurality of possible combinations and each of the initial combinations. In one example, the at least one factor is determined at the plurality of possible combinations of rotational positions and amplitudes using the at least one score at each of the combinations. In one example, there are a plurality of factors, and wherein the factors are used to determine weighted factors at the possible combinations of rotational positions and amplitudes. In one example, the next combination is determined at a best value of the weighted factors. In one example, the at least one score at each of the combinations is indicative of a patient symptom, a patient response, or a side effect to the provided stimulation. In one example, the at least one set of directional electrodes comprise split ring electrodes. In one example, the algorithm is further configured, before step (a), to determine an optimized longitudinal position for the stimulation for the patient along the lead. In one example, the optimized longitudinal position is proximate to the set of directional electrodes. In one example, the optimized longitudinal position, the optimized rotational position, and the optimized amplitude comprise optimized stimulation parameters for the patient.

BRIEF DESCRIPTION OF THE DRAWINGS

FIGS. 9A-9F show sub-steps involved in the steps shown in FIGS. 8A and 8B.

FIGS. 10-12B show steps involving how an optimal rotational angle (θopt) and an optimal amplitude (Iopt2) are determined at Lopt in a second part of the algorithm.

FIG. 14 shows a modification to the algorithm in which the clinician can enter a plurality of scores for each tested stimulation parameter set at each iteration of the algorithm.

DETAILED DESCRIPTION

Figure 5A:
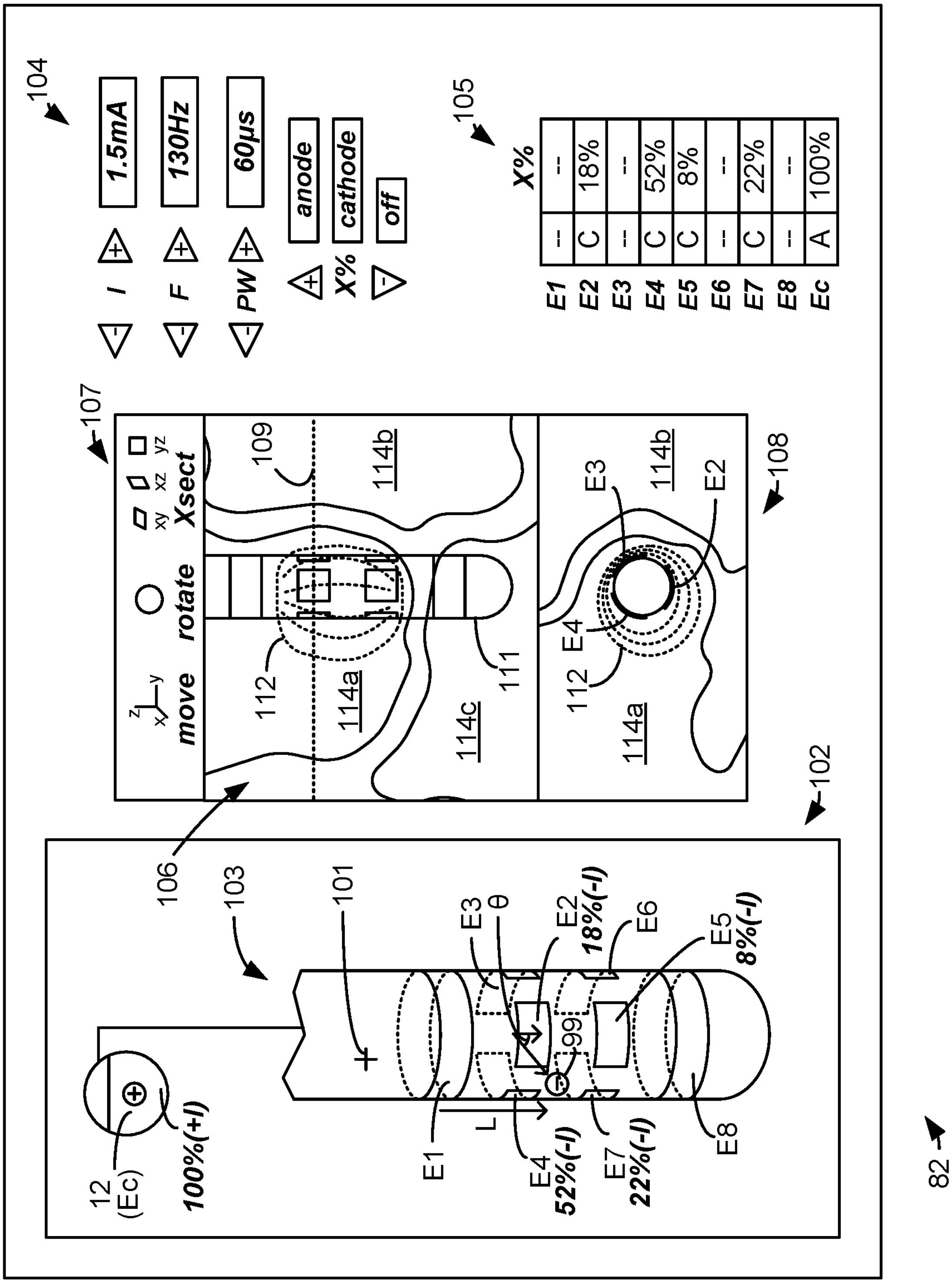
FIG. 5A shows a Graphical User Interface (GUI) operable on an external device such as a clinician programmer, which is capable of programming a stimulation program for the IPG.

FIG. 5A shows an example of GUI 82 renderable on the display 74 of the clinician program 70, which is largely borrowed from the above-incorporated '091 Publication. GUI 82 is particularly useful in an DBS context because it provides a clinician with a visual indication of how stimulation selected for a patient will interact with the brain tissue in which the electrodes are implanted. GUI 82 can be used during surgical implantation of the leads 18 or 19 and its IPG 10, but can also be used after implantation to assist in selecting a therapeutically useful stimulation program for the patient. The GUI 82 can be controlled by a cursor 101 that the user can move using a mouse connected to the clinician programmer 70 for example.

Figure 2A:
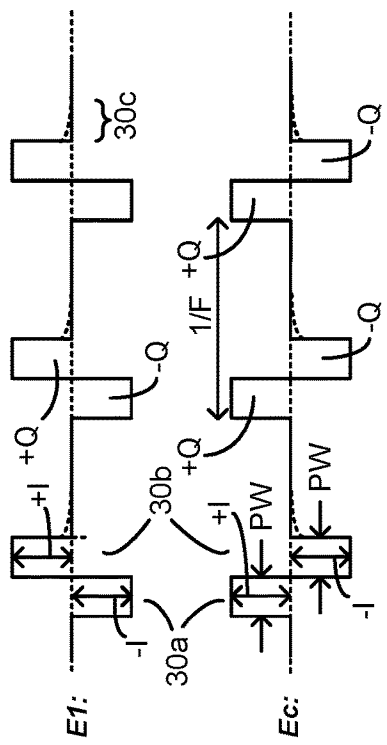
Figure 2A (prior art)
FIGS. 2A and 2B show an example of stimulation pulses (waveforms) producible by the IPG, in accordance with the prior art.
Figure 2B:
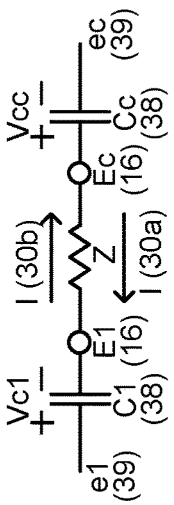
Figure 2B (prior art)

The GUI 82 may include a waveform interface 104 where various aspects of the stimulation can be selected or adjusted. For example, waveform interface 104 allows a user to select an amplitude (e.g., a current I), a frequency (F), and a pulse width (PW) of the stimulation pulses. Waveform interface 104 can be significantly more complicated, particularly if the IPG 10 supports the provision of stimulation that is more complicated than a repeating sequence of pulses. Waveform interface 104 may also include inputs to allow a user to select whether stimulation will be provided using biphasic (FIG. 2A) or monophasic pulses, and to select whether passive charge recovery will be used, although again these details aren't shown for simplicity.

Figure 3:
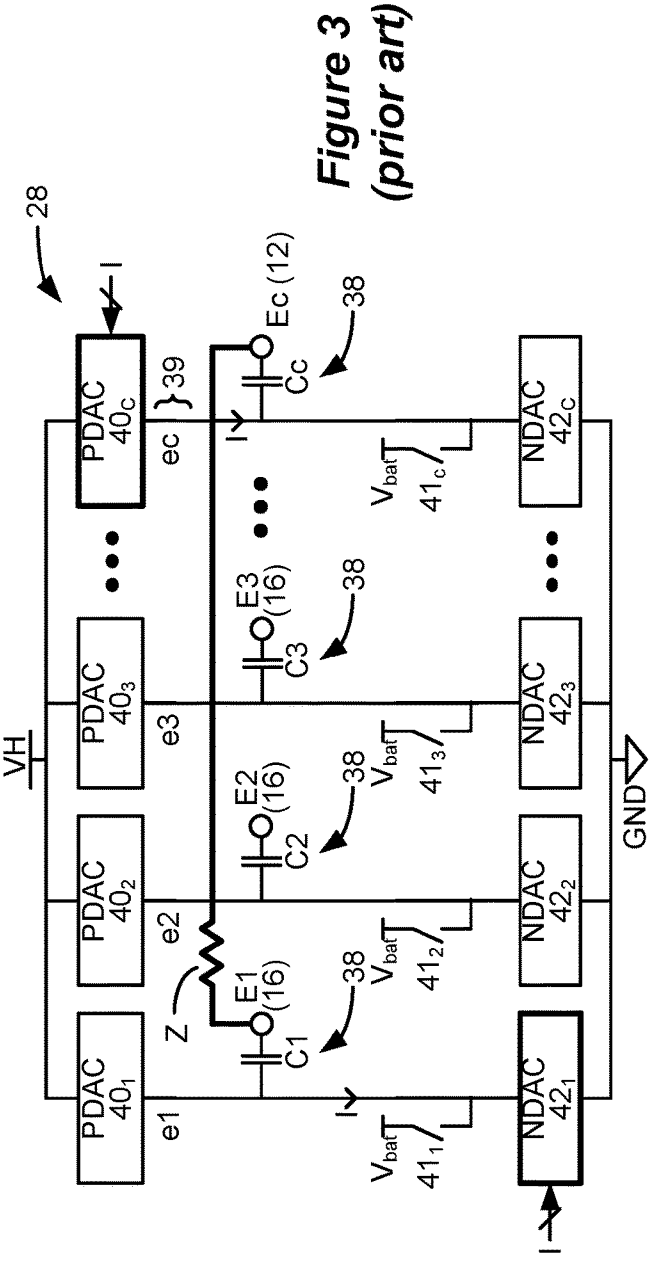
Figure 3 (prior art)
FIG. 3 shows an example of stimulation circuitry useable in the IPG, in accordance with the prior art.
Figure 5B:
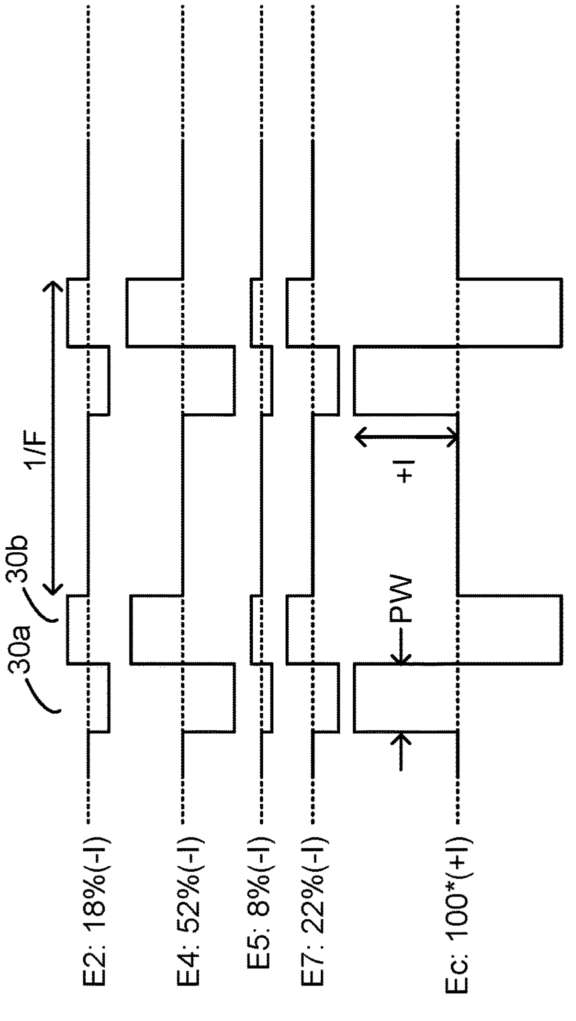
FIG. 5B shows waveforms produced at the electrodes through use of the GUI of FIG. 5A.

The GUI 82 may also include an electrode configuration interface 105 which allows the user to select a particular electrode configuration specifying which electrodes should be active to provide the stimulation, and with which polarities and relative magnitudes. In this example, the electrode configuration interface 105 allows the user to select whether an electrode should comprise an anode (A) or cathode (C) or be off, and allows the amount of the total anodic or cathodic current +I or −I (specified in the waveform interface 104) that each selected electrode will receive to be specified in terms of a percentage, X. For example, in FIG. 5A, the case electrode 12 Ec is specified to be an anode that receives X=100% of the current I as an anodic current +I (e.g., during first pulse phase 30*a* if biphasic pulses are used; see FIG. 2A). The corresponding cathodic current −I is split between cathodes electrodes E2 (18% or 0.18*−I), E4 (52% or 0.52*−I), E5 (8% or 0.08*−I), and E7 (22% or 0.22*−I) (again during first pulse phase 30*a*). The waveforms resulting at the electrodes from this electrode configuration are shown in FIG. 5B. Note that two or more electrodes can be chosen to act as anodes or cathodes at a given time, allowing the electric field in the tissue to be shaped, as explained further below. Once the waveform parameters (104) and electrode configuration parameters (105) are determined, they can be sent from the clinician programmer 70 to the IPG 10, so that the IPG's stimulation circuitry 28 (FIG. 3) can be programmed (the various NDACs and PDACs) to produce the desired currents at the selected electrodes with the proper timing. For example, PDAC 40*c* would be programmed to produce +100%*+I, and NDAC 424 would be programmed to produce 52%*−I, etc. Together, the various waveform parameters and electrode configuration parameter comprise stimulation parameters, which together comprise a stimulation program.

Use of these electrodes to provide cathodic stimulation sets a particular position for a cathodic pole 99 in three-dimensional space. The position of this cathode pole 99 can be quantified at a particular longitudinal position L along the lead (e.g., relative to a point on the lead such as the longitudinal position of electrode E1), and at a particular rotational angle θ (e.g., relative to a particular angle on the lead such as relative to the center of electrode E2). (Note that rotation angle θ is only relevant when a directional lead such as 19 (FIG. 1C) is used). This position is shown in a leads interface 102 of the GUI 82. Notice that the position of the pole 99 (L,θ) may be virtual; that is, the position may not necessarily occur at the physical position of any of the electrodes 16 in the electrode array, as explained further later. The leads interface 102 preferably also includes an image 103 of the lead being used for the patient. Although not shown, the leads interface 102 can include a selection to access a library of relevant representations 103 of the types of leads (e.g., 18 or 19) that may be implanted in different patients, which may be stored with the CP software 84. The cursor 101 can be used to select an illustrated electrode 16 (e.g., E1-E8, or the case electrode Ec), or a pole such as cathode pole 99.

An electrode configuration algorithm (not shown), operating as part of CP software 84, can determine a position of the cathode pole 99 in three-dimensional space from a given electrode configuration, and can also determine an electrode configuration from a given position of the pole 99. For example, the user can place the position of the pole 99 using the cursor 101. The electrode configuration algorithm can then be used to compute an electrode configuration that best places the pole 99 in this position. Note that cathode pole 99 is positioned closest to electrode E4, but is also generally proximate to electrodes E2, E7, and E6. The electrode configuration algorithm may thus calculate that electrode E4 should receive the largest share of cathodic current (52%*−I), while E2, E7, and E6 which are farther away from the pole 99 receive lesser percentages, as shown in the stimulation parameters interface 104. By involving more than one electrode, cathode pole 99 is formed as a virtual pole not as the position of any of the physical electrodes. Again, the electrode configuration algorithm can also operate in reverse: from a given electrode configuration, the position of the pole 99 can be determined. The electrode configuration algorithm is described further in U.S. Patent Application Publication 2019/0175915, which is incorporated herein by reference.

GUI 82 can further include a visualization interface 106 that allows a user to view a stimulation field image 112 formed on a lead given the selected stimulation parameters and electrode configuration. The stimulation field image 112 is formed by field modelling in the clinician programmer 70, as discussed further in the '091 Publication. The visualization interface 106 preferably, but not necessarily, further includes tissue imaging information 114. This tissue imaging information 114 is presented in FIG. 5A as three different tissue structures 114*a*, 114*b* and 114*c* in FIG. 6 for the patient in question, which tissue structures may comprise different areas of the brain for example. Such tissue imaging information may come from a Magnetic Resonance Image (MM) or Computed Tomography (CT) image of the patient, may come from a generic library of images, and may include user defined regions. The GUI 82 can overlay the lead image 111 and the stimulation field image 112 with the tissue imaging information 114 in the visualization interface 106 so that the position of the stimulation field 112 relative to the various tissue structures 114*i* can be visualized. The various images shown in the visualization interface 106 (i.e., the lead image 111, the stimulation field image 112, and the tissue structures 114*i*) can be three-dimensional in nature, and hence may be rendered to allow such three-dimensionality to be better appreciated by the user, such as by shading or coloring the images, etc. A view adjustment interface 107 may allow the user to move or rotate the images, using cursor 101 for example, as explained in the '091 Publication. In FIG. 5A, a cross-section interface 108 allows the various images to be seen in a particular two-dimensional cross section, and in this example a cross section 109 is shown taken perpendicularly to the lead image 111 and through split-ring electrodes E2, E3, and E4.

The GUI 82 of FIG. 5A is particularly useful because it allows the electric field as reflected in stimulation field image 112 to be seen relative to surrounding tissue structures 114*i*. This allows the user to adjust the stimulation parameters to recruit, or avoid recruiting, particular tissue structures 114*i*. Assume for example that it is desirable for a given patient to stimulate tissue structure 114*a*, but to not stimulate tissue structures 114*b* or 114*c*. This may be because tissue structure 114*a* is causing undesired patient symptoms (e.g., tremor) that stimulation can alleviate, while stimulation of tissue structures 114*b* and 114*c* will cause undesired side effects. The clinician can then use GUI 82 to adjust stimulation (e.g., to adjust the stimulation parameters or the electrode configuration) to move the stimulation field 112 (e.g., the cathode pole 99) to a proper position (L, θ). In the example shown, and as best seen in the cross-section interface 108, higher cathodic currents are provided at split-ring electrodes E4 (0.52*–I) and E2 (0.18*–I) because these electrodes are generally facing towards tissue structure 114*a* which should be stimulated. By contrast, split-ring electrode E3 carries no cathodic current because it generally faces towards tissue structure 114*b* where stimulation is ideally avoided. The result is a stimulation field 112 that is more predominant in tissue structure 114*a* and less predominant in tissue structure 114*b*, as shown in the visualization interface 106.

Especially in a DBS application, it is important that correct stimulation parameters be determined for a given patient. Improper stimulation parameters may not yield effective relief of a patient's symptoms, or may cause unwanted side effects. To determine proper stimulation, a clinician typically uses GUI 82 to try different combinations of stimulation parameters. This may occur, at least in part, during a DBS patient's surgery when the leads are being implanted. Such intra-operative determination of stimulation parameters can be useful to determine a general efficacy of DBS therapy. However, finalizing stimulation parameters that are appropriate for a given DBS patient typically occurs after surgery after the patient has had a chance to heal, and after the position of the leads stabilize in the patient. Thus, at such time, the patient will typically present to the clinician's office to determine (or further refine) optimal stimulation parameters during a programming session.

Gauging the effectiveness of a given set of stimulation parameters typically involves programming the IPG 10 with that set, and then reviewing the therapeutic effectiveness and side effects that result. Therapeutic effectiveness and side effects are often assessed by one or more different scores (S) for one or more different clinical responses, which are entered into the GUI 82 of the clinician programmer 70 where they are stored with the stimulation parameters set being assessed. Such scores can be based on patient or clinician observations. For example, bradykinesia (slowness of movement), rigidity, tremor, or other symptoms or side effects, can be scored by the patient, or by the clinician upon observing or questioning the patient. Scores can also be objective in nature based on measurements taken regarding a patient's symptoms or side effects. For example, a Parkinson's patient may be fitted with a wearable sensor that measures tremors, such as by measuring the frequency and amplitude of such tremors. A wearable sensor may communicate such metrics back to the GUI 82, and if necessary convert to a score. U.S. Patent Application Publication 2021/0196956, which is incorporated herein by reference in its entirety, discusses determining which symptoms and/or side effects are most sensible to score for a given patient when the stimulation parameters are optimized.

Once the GUI 82 of the clinician programmer 70 has received various scores (whether subjective or objective, and whether from patient or clinician) for each of the sets of stimulation parameters tested, the clinician may review the scores to try and determine one or more sets of optimal stimulation parameters for the patient which maximize therapeutic effectiveness while minimizing unwanted side effects. Typically, this process involves significant guess work and time, especially when a directional lead (e.g., FIG. 1C) is used. If testing all possible stimulation parameter sets is done as comprehensively as possible, stimulation would need to be provided to the patient at every possible stimulation position (L, θ). Then different combinations of the waveform parameters (e.g., F, PW, and I) would be tested at each of these positions, and then scored (S). In reality, it may only be necessary to optimize the waveform parameter of amplitude (I), as other parameters (F, PW) may be known or determined by other means. In short, a data set (I, L, θ, S) would need to be determined for all possible combinations of I, L and θ the IPG 10 is capable of producing. This may be a burdensome number of combinations to try during a programming session. At any given combination of I, L and θ, it may take some time (e.g., a matter of minutes) to determine an appropriate score (S), because the patient may need to be observed, may need to perform certain tasks (finger tapping, walking, etc.), or may need to answer a number of questions. Because a programming session may only reasonably last a few hours, only a fraction of possible I, L and θ combinations can be tested and scored.

Figure 1A:
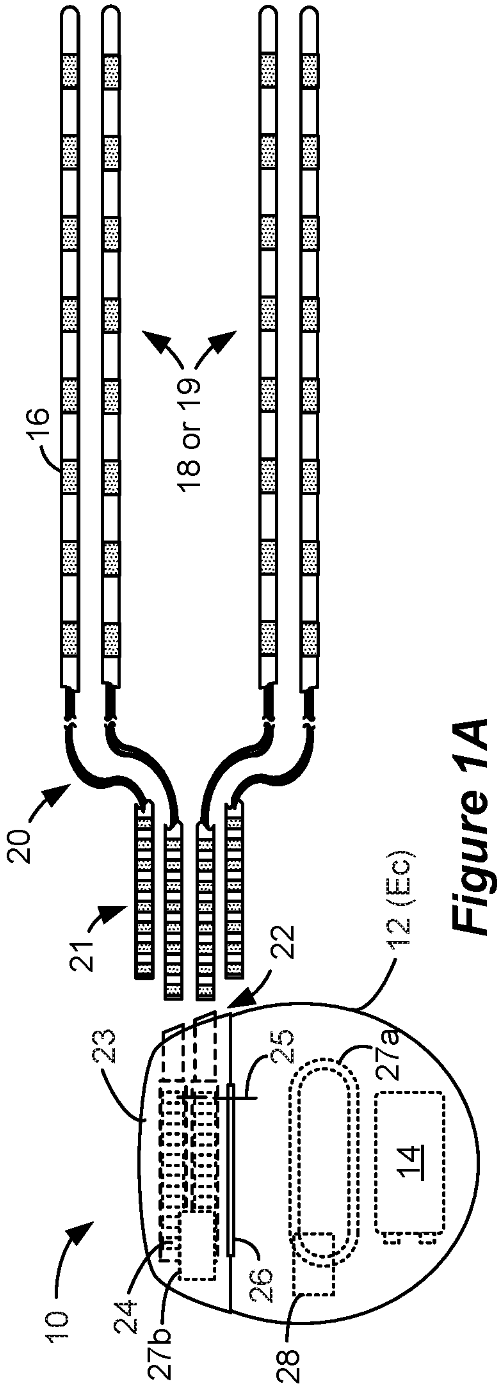
Figure 1A (prior art)
FIG. 1A shows an Implantable Pulse Generator (IPG), in accordance with the prior art.
Figure 1B:
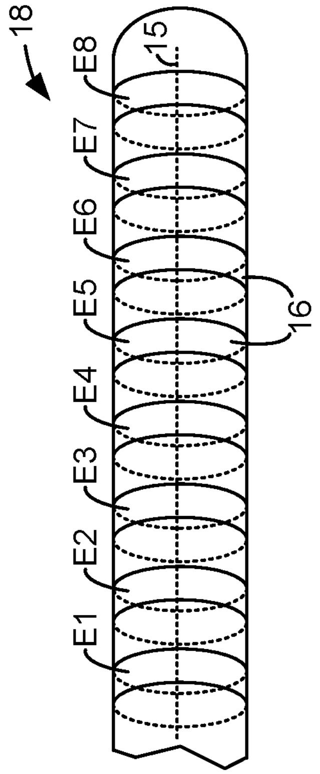
Figure 1B (prior art)
FIG. 1B shows a percutaneous lead having ring electrodes.
Figure 1C:
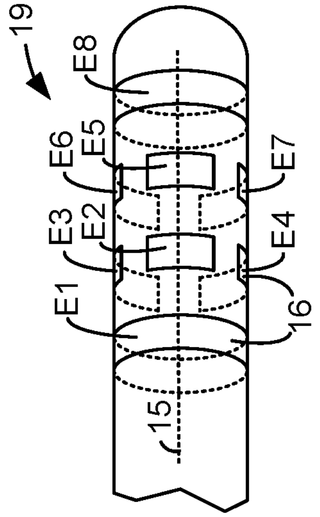
Figure 1C (prior art)
FIG. 1C shows a percutaneous lead having split ring electrodes, in accordance with the prior art.

To address this concern, the inventors have developed a new programming algorithm to efficiently test different I, L and θ combinations with the goal of more quickly arriving at optimal stimulation parameters for a given patient having a directional lead (e.g., FIG. 1C). Another waveform parameter (e.g., F, PW) could also be optimized along with stimulation positioning data L and θ, but the waveform parameter of amplitude (I) is chosen for optimization given its high significance to patient treatment.

Figure 6:
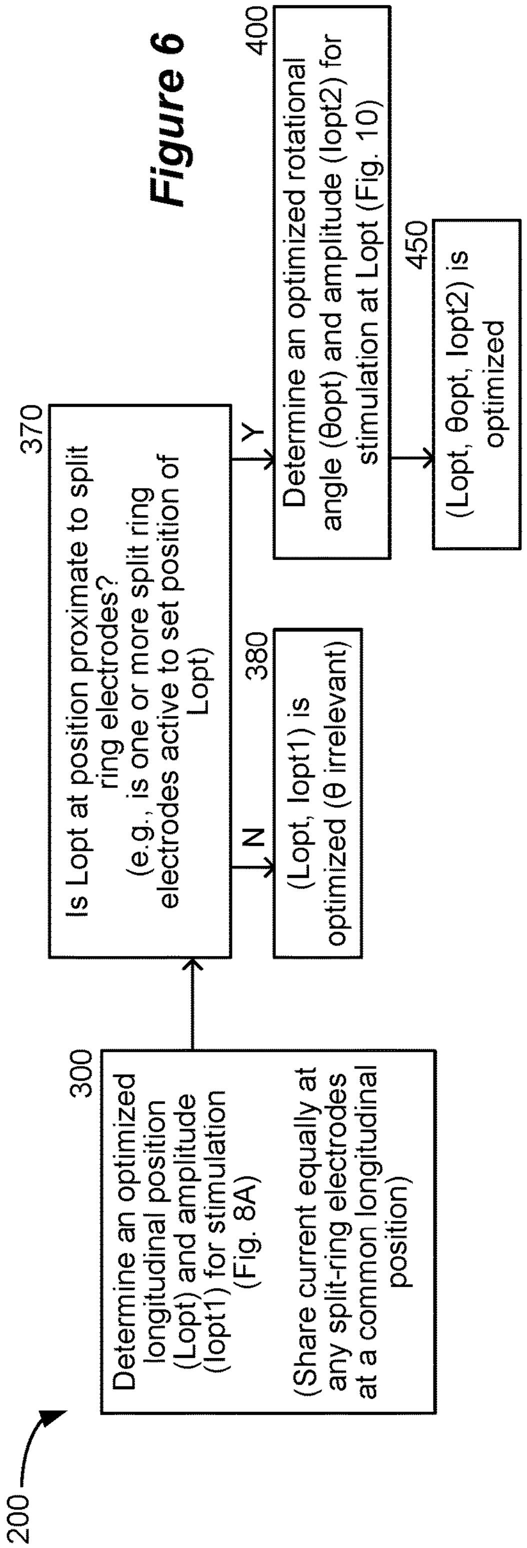
FIG. 6 shows a programming algorithm for optimizing stimulation in a patient, including the ability to determine an optimal longitudinal position and rotational angle of the stimulation, as well as an optimal amplitude.

This programming algorithm 200 is shown at a high level in FIG. 6, with other sub-steps and details shown in subsequent figures. The algorithm 200 preferably first simultaneously determines an optimal longitudinal position (Lopt) and amplitude (Iopt1) for stimulation (300) along the lead. When determining Lopt and Iopt1, stimulation is positioned symmetrically (non-directionally) around the lead by setting currents equal at split ring electrodes at a common longitudinal position. As explained further below, determining Lopt and Iopt1 involves the algorithm 200 efficiently selecting various values for L and I (L,I) at which stimulation can be tried on the patient and scored. This is an iterative process, and the algorithm 200 automatically determines a next (L,I) value to be tested and scored based on previously tested and scored (L,I) values.

Once Lopt is determined, the algorithm 200 determines whether Lopt is proximate to split ring electrodes (370)—i.e., whether Lopt is longitudinally at or close to split ring electrodes on the directional lead. Lopt may be determined to be proximate to split ring electrodes if at least one split ring electrode is used (active) to set the position of Lopt, as explained further below. If Lopt is not proximate to split ring electrodes, Lopt and Iopt1 are optimized for the patient (380), and providing stimulation directionally at a rotational angle θ is irrelevant and thus not optimized.

If Lopt is proximate to split ring electrodes (370), the algorithm 200 simultaneously determines an optimal rotational angle (θopt) and amplitude (Iopt2) for stimulation around the lead at the optimized longitudinal position Lopt (400). Algorithm 200 may determine that Iopt2 is the same as Iopt1 determined earlier, but it is also likely that Iopt2 will differ from Iopt1 as the rotational angle of stimulation is also optimized. As explained further below, determining θopt and Iopt2 involves the algorithm 200 selecting various values for θ and I (θ,I) which can be tried on the patient and scored. This process can be similar to the manner in which (L,I) values were selected earlier, with the algorithm 200 automatically and efficiently determining next (θ,I) values to be tested and scored based on previously tested and scored (θ,I) values. Once θopt and Iopt2 are optimized, the stimulation is fully optimized for the patient, as the longitudinal position, rotational angle, and amplitude of the stimulation (Lopt, θopt, Iopt2) have now been determined (450).

Figure 4:
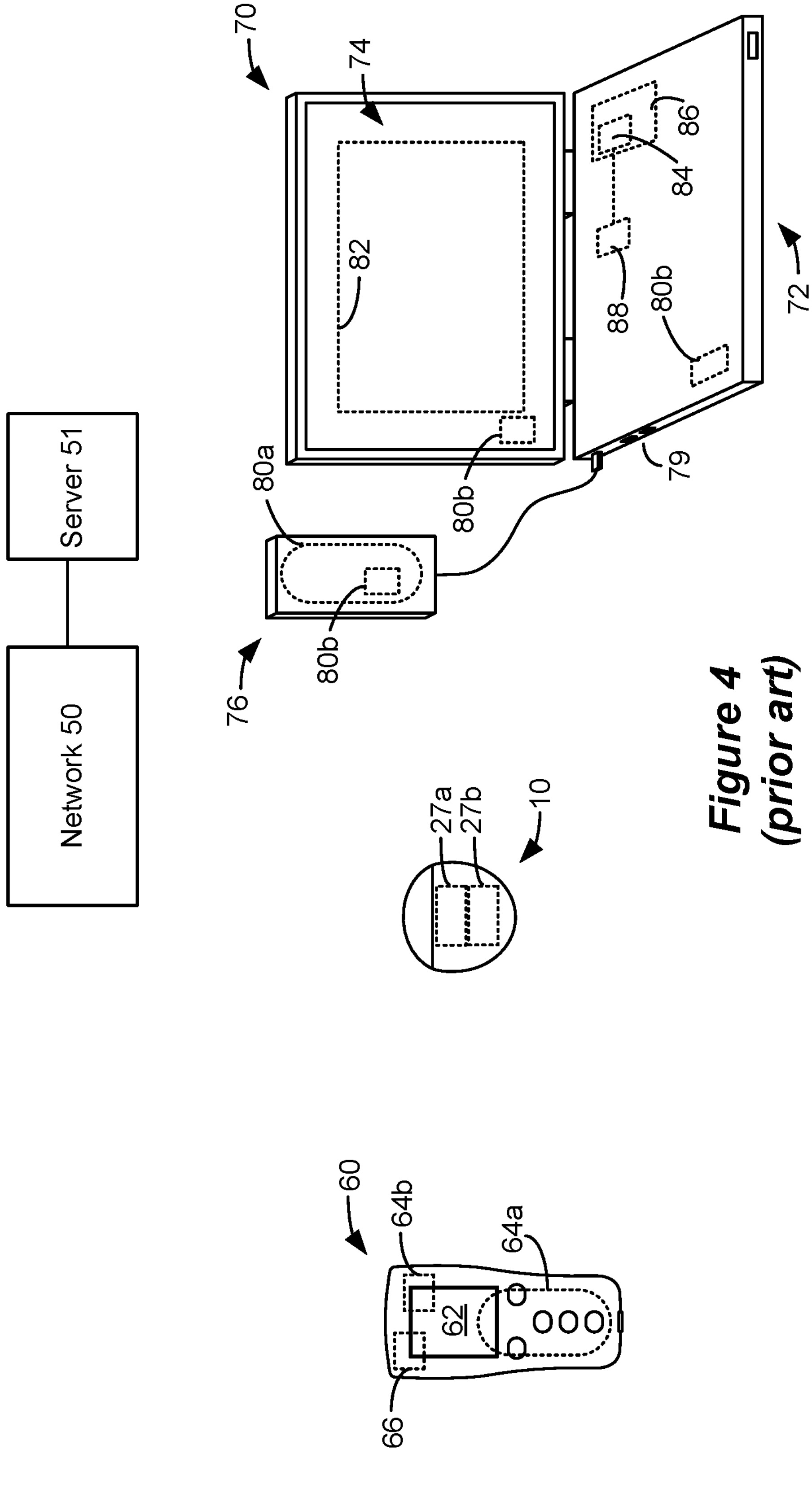
Figure 4 (prior art)
FIG. 4 shows various external devices capable of communicating with and programming stimulation in an IPG, in accordance with the prior art.
Figure 13:
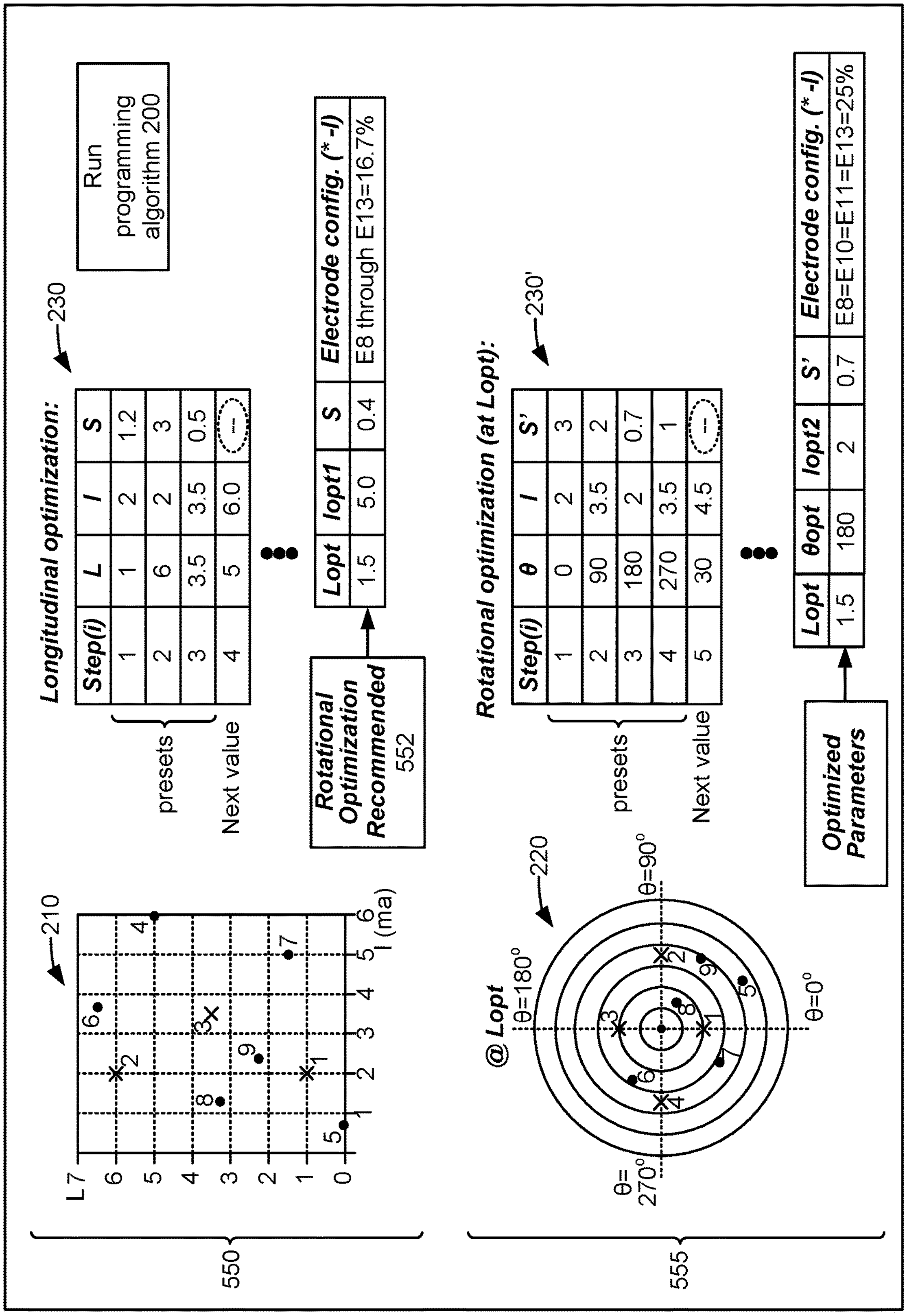
FIG. 13 shows the GUI that may be used to implement the programming algorithm, and to display information that may be useful to the clinician as the algorithm operates.

One skilled in the art will appreciate that programming algorithm 200 can comprise a portion of software 84 operable in the clinician programmer 70. FIG. 13, described later, shows how the GUI 82 of the clinician programmer 70 can be used to run the algorithm 200, to record measurements (e.g., scores) taken during execution of the algorithm 200, and to display useful information to the clinician. While use of algorithm 200 is preferred on the clinician programmer 70 and is so shown in subsequent examples, algorithm 200 can run on any external system used to control and program the IPG 10. Algorithm 200 may also operate on any external device (such as network 50 or server 51; FIG. 4) that is in communication (either directly or by a network such as the Internet) with another external device (such as clinician programmer 70 or patient controller 60) capable of controlling stimulation at the IPG 10. Furthermore, the algorithm 200 can operate on an external device that doesn't control the IPG 10, or that is not in communication with another external device that controls the IPG. For example, the algorithm 200 can operate on a first external system, with outputs from the algorithm (e.g., stimulation parameter sets) manually entered into a second external system that controls the IPG 10. Again in the examples that follow, it is assumed for simplicity that the algorithm 200 operates on the clinician programmer 70. Algorithm 200 can be stored as instructions on a computer-readable medium, such as on a magnetic or optical disk, in solid state memory, etc., and may be so stored in the clinician programmer 70 or in any external system such as those just mentioned.

Figure 7:
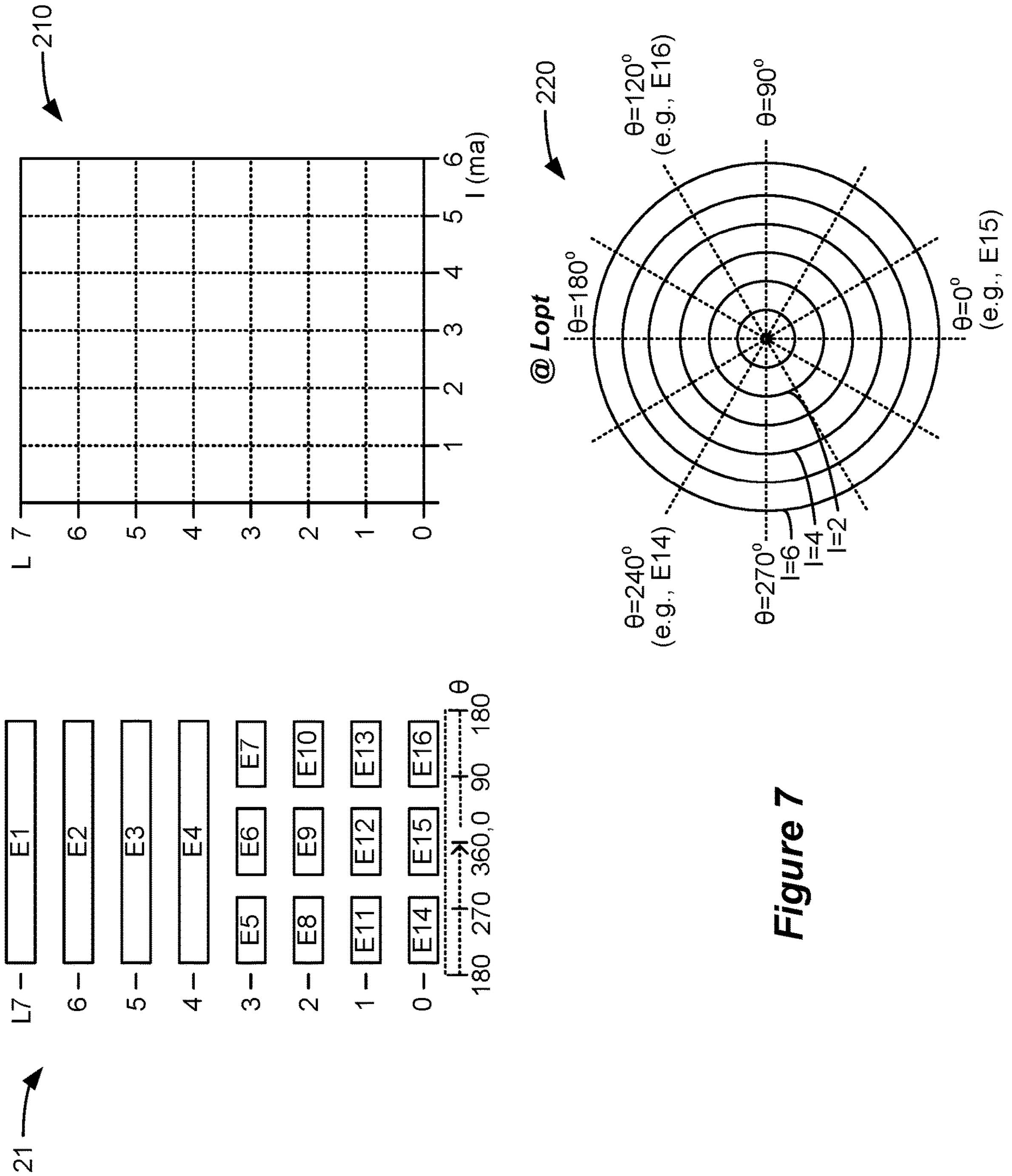
FIG. 7 shows an example of a GUI representation of a lead for which stimulation is optimized, and further shows parameters spaces useful to understanding the algorithm.

FIG. 7 shows various representations that are useful in understanding the description of programming algorithm 200 that follows. First, a directional lead 21 is illustrated in a two-dimensional manner. As shown, this directional lead 21 includes ring electrodes E1-E4 which are respectively located at longitudinal positions (L) 7, 6, 5, and 4, and split ring electrodes E5-E16 which are located at longitudinal positions (L) 3, 2, 1, and 0 as shown. L can also be represented by an actual physical measurement, such as millimeters. Rotational angle θ around the lead 21 is also shown, with 0 degrees being selected at some arbitrary position (such as in the middle of split ring electrodes E6, E9, E12, and E15). Of course, this type of directional lead 21 is just one example, and other directional leads having different combinations of ring and split ring electrodes, or directional leads having split ring electrodes exclusively, could be used as well. As discussed further below, at least parts of algorithm 200 may operate with non-directional leads as well.

L,I parameter space 210 shows possible values (L,I) that can be tested and optimized, which is particularly useful during step 300 (FIG. 6) when Lopt and Iopt1 are determined. L,I parameter space 210 can have any resolution that the IPG 10 is capable of producing. For example, it can be assumed in one example that the amplitude I of the current is adjustable in increments of 0.1 mA, up to a maximum of 6.0 mA. Longitudinal position L may also be set in increments of tenths.

Parameter space 220 shows possible values for (θ,I) that can be tested and optimized, which is particularly useful during step 400 (FIG. 6) when θopt and Iopt2 are determined at the already-established position of Lopt. θ,I parameter space 220 as shown is circular, with rotational angle θ represented angularly, and with amplitude I represented radially. Parameter space 220 can again have any resolution that the IPG 10 is capable of producing. For example, it can be assumed in one example that the rotational angle θ is adjustable in increments of 30° degrees, and again the amplitude I of the current is adjustable in increments of 0.1 mA up to a maximum of 6.0 mA.

Figure 8A:
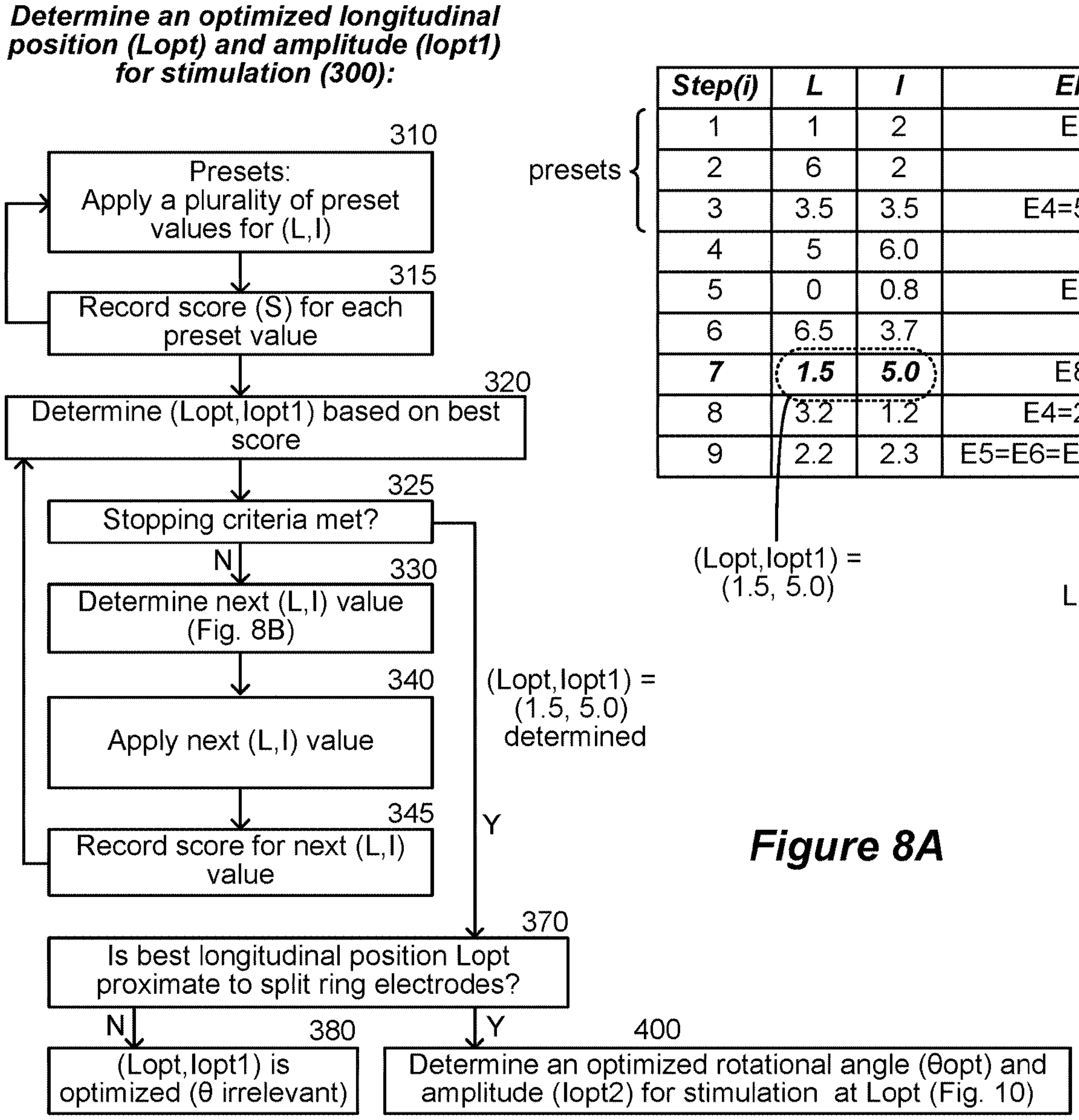
FIGS. 8A and 8B show steps involving how an optimal longitudinal position (Lopt) and an optimal amplitude (Iopt1) are determined in a first part of the algorithm.
Figure 8A:
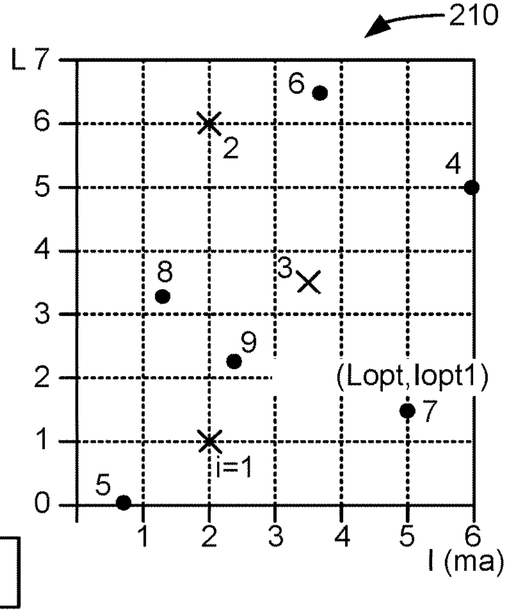

FIG. 8A shows steps involved in determining Lopt and Iopt1 (300). See also U.S. Patent Application Publication 2018/0104500, which is incorporated by reference it its entirety. Preferably, the algorithm 200 uses a plurality of preset (L,I) values at its inception (310). These preset values will depend on the type of lead for which stimulation is being optimized, and are preferably chosen to cover a desired portion of the lead to be searched, and/or the most probable position of optimal stimulation. In the example shown, three presets are used with (L,I) values of (1, 2 mA), (6, 2 mA) and (3.5, 3.5 mA), which are sequentially selected in different steps (i=1, 2, and 3) and applied to the patient. As explained further below, applying (L,I) values involves the clinician programmer 70 transmitting stimulation parameter sets (as reflected in the electrode configuration) to the IPG 10 so that stimulation can be produced at the prescribed position (L) and amplitude (I).

Data set 230 is formed in the clinician programmer 70 as the algorithm 200 runs, and includes the electrode configurations necessary to form stimulation at the prescribed longitudinal positions, L. For example, and referring to illustration of lead 21 in FIG. 7, notice that longitudinal position L=1 (step i=1 for the first preset value) corresponds to the location of split ring electrodes E11, E12, and E13. Because step 300 only seeks to determine L and I without imparting any directionality (rotation) to the stimulation (i.e., such that the stimulation field 112 is symmetric around the lead), these electrodes E11, E12, and E13 will share the cathodic current equally (33%*–I), effectively placing cathodic pole 99 longitudinally at L=1. More specifically, because I=2 mA at this step i=1, each of electrodes E11, E12, and E13 will receive −0.67 mA at this step. (Note that the actual current provided at the active electrodes may depend upon the resolution providable by the IPG 10. For example, if the IPG 10 can provide current in 0.1 mA increments, each of the electrodes E11, E12, and E13 may receive 0.7 mA, i.e., 0.67 mA rounded to the nearest tenth).

Longitudinal position L=6 (step i=2 for the second present value) corresponds to the location of ring electrode E2, which will receive 100% of the cathodic current (100%*–I) to place cathode pole 99 longitudinally at this position. More specifically, because I=2 mA at this step i=2, electrode E2 will receive −2.0 mA at this step.

Longitudinal position L=3.5 (step i=3 for the third preset value) is directly between ring electrode E4, and the longitudinal position of split ring electrodes E5, E6, and E7. Therefore, to place the cathode pole 99 (virtually) as this position, the cathodic current is shared equally between E4 (50%*–I) and E5, E6, and E7 as a group (with each receiving 16.7%*–I). More specifically, because I=3.5 mA at this step i=3, each of electrode E5, E6, and E7 will receive −0.6 mA at this step (rounded), with E4 receiving 1.7 mA (rounded to give a sum total of 3.5 mA). Although not shown, remember that these electrode configurations as reflected in data set 230 are determinable in the CP software 84 using the electrode configuration algorithm described earlier, which can comprise a portion of programming algorithm 200.

The stimulation parameters as embodied in the (L,I) presets and as determined by the electrode configuration algorithm (the active electrodes; whether they are anodes or cathodes, and the amplitude at each active electrode) are sequentially transmitted to the patient's IPG 10 (along with other non-optimized parameters such as frequency F and pulse width PW) so that the stimulation can be applied to the patient. As each of these stimulation parameters sets are applied, at least one score (S) is then determined for each (315). As noted above, a score can comprise any metric (subjective or objective) that indicates therapeutic effectiveness of and/or the side effects resulting from the stimulation parameters sets. In the example shown, it is assumed that a lower score indicates a better result, with 0 being good and 4 poor, although a different scale could be used in which higher numbers are better. The scores (S) once determined for each of the presets are entered into the data set 230 in the clinician programmer 70, such as by having the clinician type the score into the GUI 82 (see FIG. 13). Scores can also automatically be populated into the data set 230 if they are objectively measured and determined, using sensors and the like. In FIG. 8A, notice that the first (L,I) point (1,2) results in a score of 1.2; the second (6,2) results in a score of 3 (poor); and the third (3.5, 3.5) results in a score of 0.5 (good). As discussed later, the scores S can comprise a composite based on a number of metrics that indicate effective and/or side effects, and a plurality of scores can also be determined at each (L,I) value, but this detail is not yet shown for simplicity.

After sequentially applying stimulation according to these presets and determining and recording their scores S after patient testing, the programming algorithm 200 can determine a best of the (L,I) values (Lopt, Iopt1) based on the scores at those points (320). As explained further below, as the algorithm 200 iterates, more (L,I) values will be tested and scored, and (Lopt, Iopt1) can be updated accordingly at this step. At this point, after only testing the presets, (Lopt, Iopt1) is determined at step 320 to be (3.5, 3.5), because this tested value yields the best (e.g., lowest) score (of 0.5).

Next, the algorithm 200 determines whether one or more stopping criteria have been met (325). If a stopping criterium has been met (325), the algorithm 200 may stop determining and testing further (L,I) values, and at this point (Lopt, Iopt1) are established. Any number of stopping criteria can be used. For example, the algorithm 200 may decide to stop: if a last determined (L,I) value is too close to other values that have been tested. (Note that a different distance equation and/or weighting could be used for a stopping determination versus a next-point prediction determination as described further below); if the scores at a number of proceeding values are poor (suggesting that the algorithm is no longer suggesting new (L,I) values to useful effect); if a score at the last selected value is significantly good (suggesting that the algorithm can simply select this last value as the optimal point); if a maximum number of steps (i) has been reached; etc. The stopping criteria need not be automated in the algorithm 200. For example, a stopping criterium may simply comprise the clinician deciding that no further steps are required.

If a stopping criteria has not been met (325), the algorithm 200 proceeds to determine a next (L,I) value to be tested (330) in a next iteration (step i=4). Details involved in choosing this next (L,I) value are shown first with respect to FIG. 8B. The algorithm 200 computes and considers one or more factors, and the illustrated example considers four factors $R_A$, $R_B$, $R_C$, $R_D$, although more or fewer factors could be used. Each of these factors is preferably calculated at all possible (L,I) points (332-335) in the L,I parameter space 210, although certain (L,I) values can also be excluded (337), as explained further below. Factors R may be determined based on the distance to all previously-tested (L,I) values, the scores S at those points, or based on other considerations explained further below. When more than one factor is used, the factors can be weighted (which can include normalizing or ranking, as explained further below) and summed ($R_W$; 336) at each (L,I) value, as explained further below. A next (L,I) value to be tested can be determined by picking the weighted factor $R_W$(L,I) having the best (e.g., lowest) value (338), again as explained in further detail below.

Step 332 calculates factor $R_A$ for all (L,I) positions using an inverse distance metric, as shown in FIG. 9A. The calculated value for $R_A$ at each (L,I) position in L,I parameter space 210 is represented by data set 240, which is determined and stored in the clinician programmer 70 (or other external device) as the algorithm 200 runs. Note that the number of entries comprising $R_A$ data set 240 depends on the resolution at which both I (e.g., 0.1 mA) and L (e.g., in tenths) are defined in the system, as well as the extent to which L,I parameter space 210 is searched. The equation for calculating $R_A$ at each (L,I) point in data set 240 is shown in FIG. 9A. Note that factor $R_A$ relies on both the previous position of previously-tested (L,I) values (in steps i=1-3) as reflected in the inverse distance $1/d_j$ from each (L,I) point to the previously-tested points. $R_A$ also relies on the scores $S_i$ ($S_1$, $S_2$, $S_3$) at each of those previously-tested points. In this example, (L,I) values having lower values for $R_A$ are more likely to selected as a next (L,I) value to test, as explained further below.

Note as shown in the equation in FIG. 9A that distance d can be determined in a Euclidian fashion, and can comprise the square root of the sum of the differences (in L and I) squared. However, distance could be computed in other fashions. For example, stimulation field modelling (SFM) can be used to model a volume of activation (VOA) in the tissue both at a given (L,I) point and each of the previously-tested points, with a centroid or some other relevant point within those VOA used to determine the distances. SFM modelling may also be beneficial to determining whether stimulation will overlap with an exclusion zone, as discussed further below with respect to FIG. 9F. Variable 'p' represents a power parameter that tends to accentuate the distances $d_i$ and can be empirically set (e.g., to 5 in one example). In effect, factor $R_A$ comprises an estimated or predicted score at other (L,I) values that have not yet been tested, and such estimated or predicted scores are based upon the scores at previously-tested positions, as well as the inverse distances to those points. Note that actual calculated values for $R_A$ at each (L,I) point are not shown in data set 240. Different prediction-based calculations could be used to determine factor $R_A$ as well.

Figure 8B:
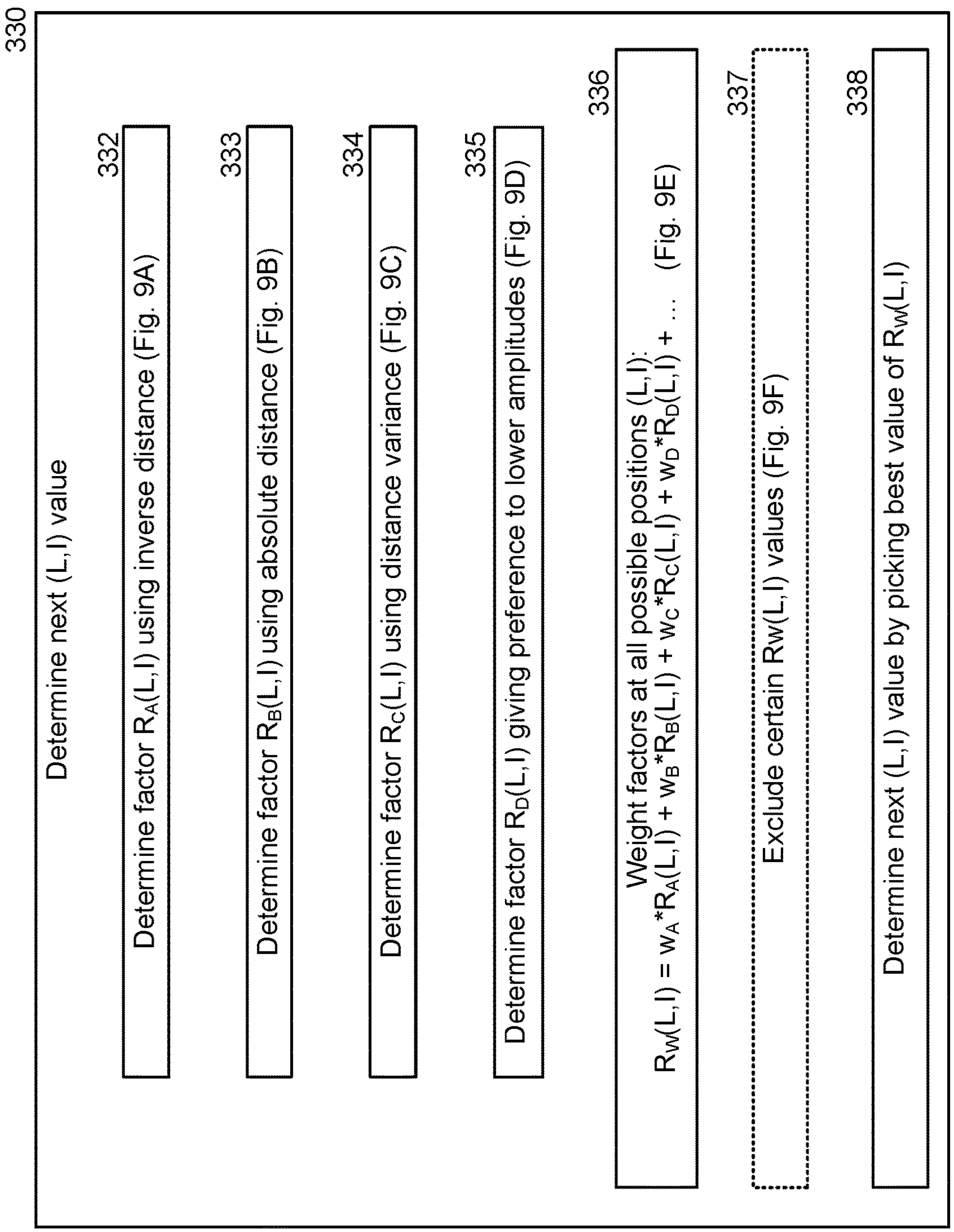
Figure 9B:
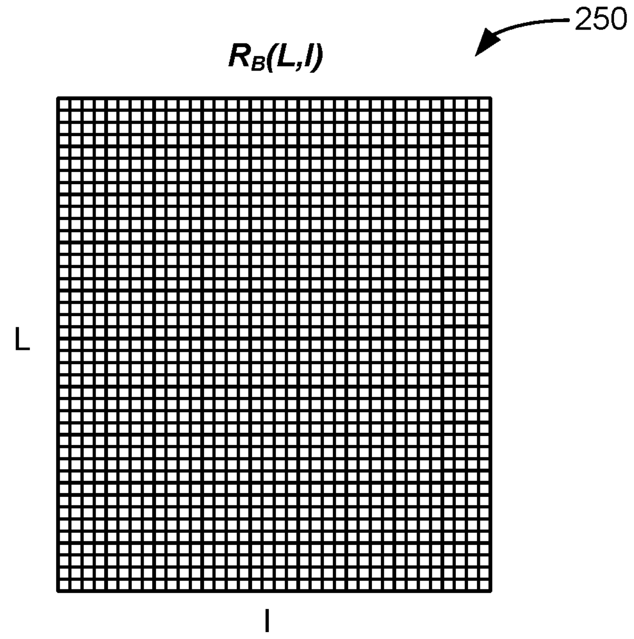
Figure 9B:
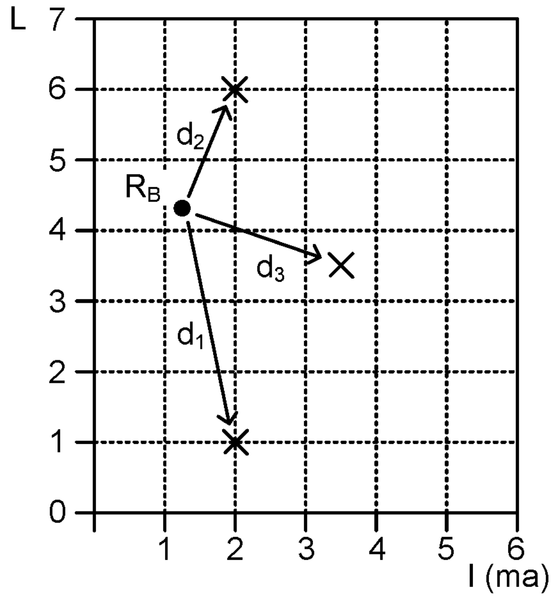

Returning to FIG. 8B, step 333 determines a second factor $R_B$ for all (L,I) positions using an absolute distance metric, as shown in FIG. 9B. This factor, generally speaking, tends to favor selection of a next (L,I) point that is furthest away from previously-tested (L,I) points, and is thus beneficial in that it encourages the algorithm to select a next (L,I) point for testing at locations in L,I parameter space 210 that haven't yet been tested. The calculated value for $R_B$ at each position (L,I) is represented by data set 250, which is determined and stored in the clinician programmer 70 as the algorithm 200 runs. The equation for calculating $R_B$ at each (L,I) point in data set 250 is shown in FIG. 9B, and comprises the sum of the distances $d_i$ from each (L,I) point to the previously tested points. Because it is desired that lower values for $R_B$ are preferred when selecting a next (L,I) value to be tested in the depicted example, this sum is made negative, such that (L,I) values with longer summed distances to previously-tested points are more likely to be selected. However, other means can be used to translate larger summed distances into lower values for $R_B$. Note that $R_B$, unlike $R_A$, does not rely on the scores $S_i$ at previously tested points. Again, actual values for $R_B$ at each (L,I) point are not shown in FIG. 9B.

Figure 9C:
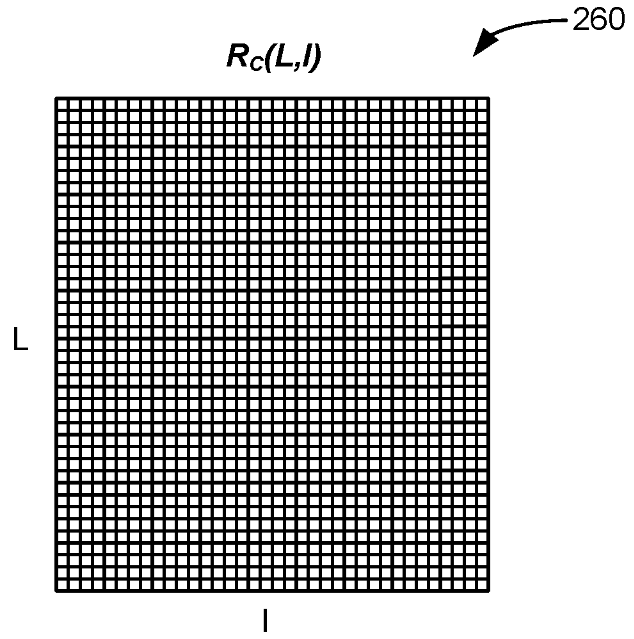
Figure 9C:
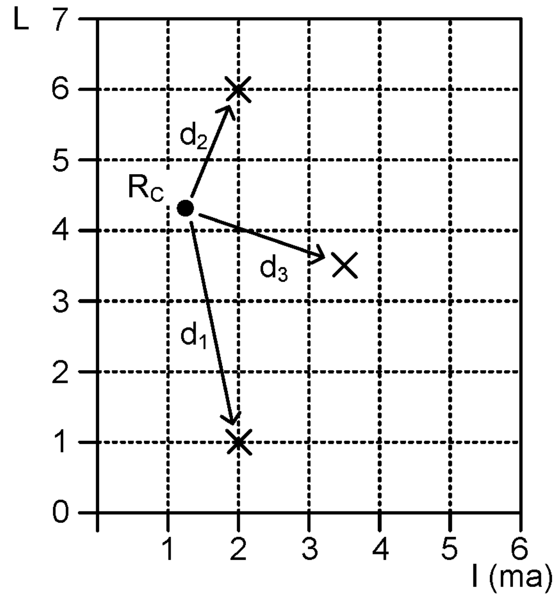

Returning to FIG. 8B, step 334 determines a third factor $R_C$ for all (L,I) positions using a distance variance metric, as shown in FIG. 9C. This factor, generally speaking, tends to favor selection of a next (L,I) point that is most equidistant from previously tested (L,I) points. The calculated value for $R_C$ at each position (L,I) is represented by data set 260, which is determined and stored in the clinician programmer 70 as the algorithm 200 runs. The equation for calculating $R_C$ at each (L,I) point in data set 240 is shown in FIG. 9C, and simply comprises the variance of the distances $d_i$ from each (L,I) point to the previously tested points, with lower values for $R_C$ indicating (L,I) points more likely to be selected as the next (L,I) value to be tested. Note that $R_C$, like $R_B$, does not rely on the scores $S_i$ at previously tested points. Again, actual values for $R_C$ at each (L,I) point are not shown in FIG. 9C.

Figure 9D:
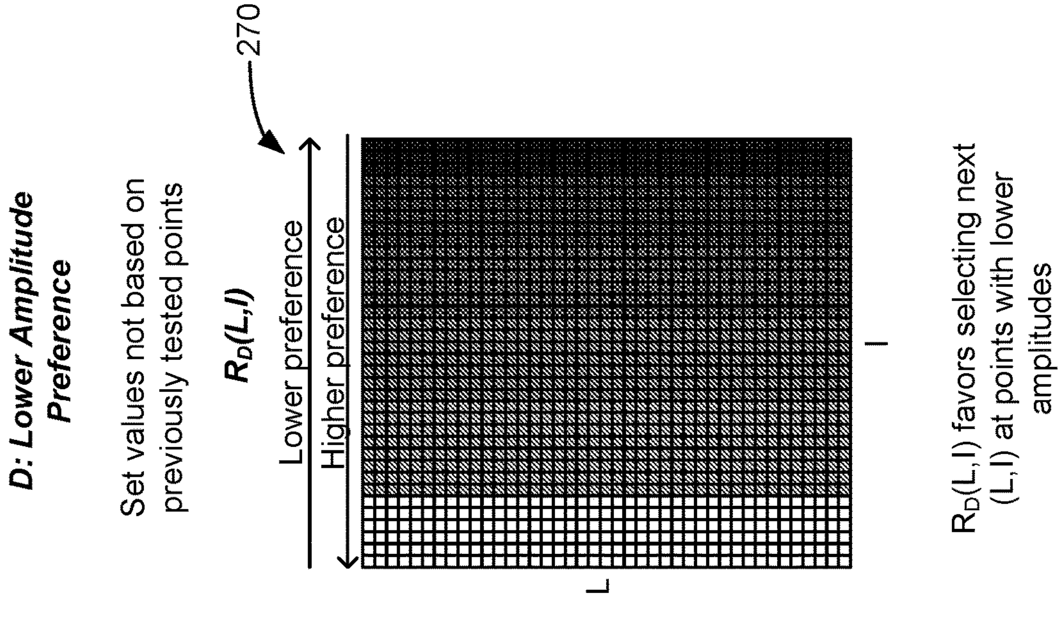

Returning to FIG. 8B, step 335 determines a fourth factor $R_D$ for all (L,I) positions using a preference for lower amplitudes, as shown in FIG. 9D. This factor, generally speaking, tends to favor selection of a next (L,I) point that has lower values of amplitude, I. This factor is reasonable to consider as it is generally preferred to provide a patient stimulation that is as low in amplitude as possible. The values for $R_D$ at each position (L,I) is represented by data set 270. This data set 270 may be preset and not based on the position of or scores at previously tested values. For example, $R_D$ may be higher at (L,I) points having higher amplitudes (e.g., $R_D=4$ when I>5 mA) and lower at (L,I) values having lower amplitudes (e.g., $R_D=0$ when I<1 mA), which biases the algorithm 200 towards selection of a next (L,I) value which is at a lower amplitude.

Algorithm 200 doesn't require the use of all of the factors described in FIGS. 9A-9D, and still other factors that aren't shown could be used as well. These factors could also be computed differently.

Returning to FIG. 8B, a weighted factor $R_W$ for all (L,I) positions is determined using the factors $R_A$, $R_B$, $R_C$, and $R_D$ determined earlier (336). In one example, weights $w_A$, $w_B$, $w_C$, and $w_D$ can be multiplied by their associated factors to yield $R_W(L,I)=w_A*R_A(L,I)+w_B*R_B(L,I)+w_C*R_C(L,I)+w_D*R_D(L,I)$. The resulting values for $R_W$ at each position (L,I) is represented by data set 280 as shown in FIG. 9E.

Figure 9E:
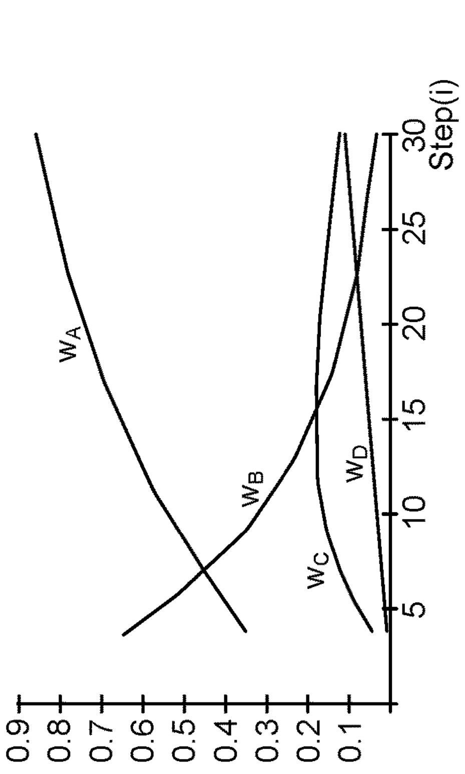
Figure 9E:
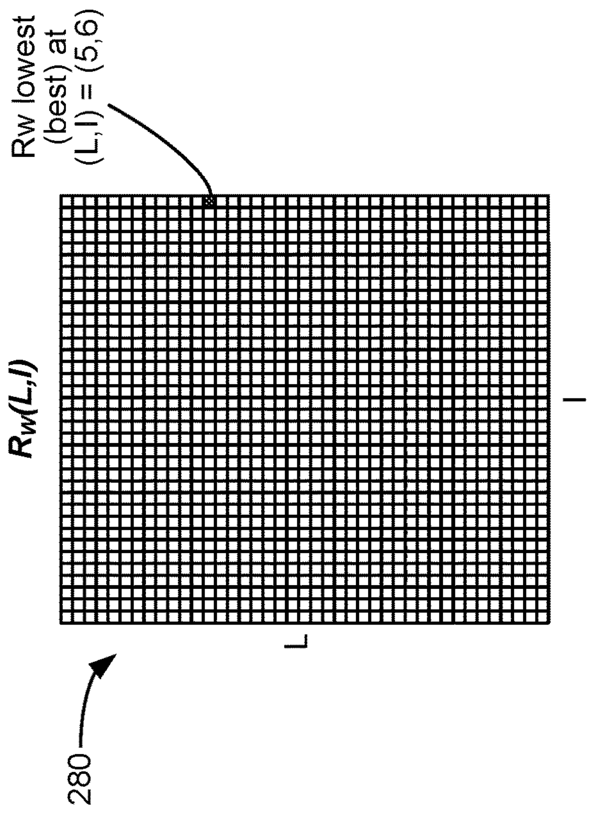

The weights w applied to the factors can be varied based on user preferences, and FIG. 9E shows example values. FIG. 9E also shows that the weights w can vary in accordance with the step number i—i.e., how many times the algorithm 200 has iterated to determine a next (L,I) value, as explained further below. For example, when initially determining a fourth (L,I) value to test after the three presets (at step i=4), it may be useful to emphasize factor $R_B$—absolute distance (FIG. 9B)—when determining $R_W$ because this factor favors choosing a next (L,I) value that is furthest from the previously-tested presets in L,I parameter space 210. During later iterations and after more (L,I) positions have been determined and scored, it may be more useful to emphasize factor $R_A$—inverse distance (FIG. 9A)—because this factor places greater weight on the scores determined at the previously-tested (L,I) values. Thus, in FIG. 9E, weight $w_A$ is lower and weight $w_B$ is higher at earlier iterations of the algorithm 200, but $w_A$ is higher and $w_B$ is lower at later iterations. Although not illustrated, weights w can also be dependent on recorded scores, or in accordance with other static or dynamic factors.

Note that weighting of the factors to arrive at $R_W(L,I)$ can involve some amount of processing of the individual factors $R_I(L,I)$. In this regard, note that each of the individual factors $R_I(L,I)$ may be of different magnitudes, depending on how such factors are computed. As such, it may be beneficial to normalize the different factors $R_I(L,I)$ so that their magnitudes are generally equated before these factors are weighted by weights $w_I$. Alternatively, the weights $w_I$ themselves may be adjusted to accomplish such normalization, so that the individual contributions provided by $w_I*R_I(L,I)$ leading to $R_W(L,I)$ are generally equal in magnitude. In another alternative, each of the (L,I) values for a given factor $R_I$ can be ranked, with for example a best (lowest) value (L,I) being given a best (e.g., lowest) ranking (e.g., 1), and a worst (highest) value (L,I) being given a worst (highest) ranking (e.g., L*I). Ranking each (L,I) value for each factor $R_I$ before weighting tends to normalize the values of each of the factors, making their weighting by $w_I$ more meaningful.

Figure 9F:
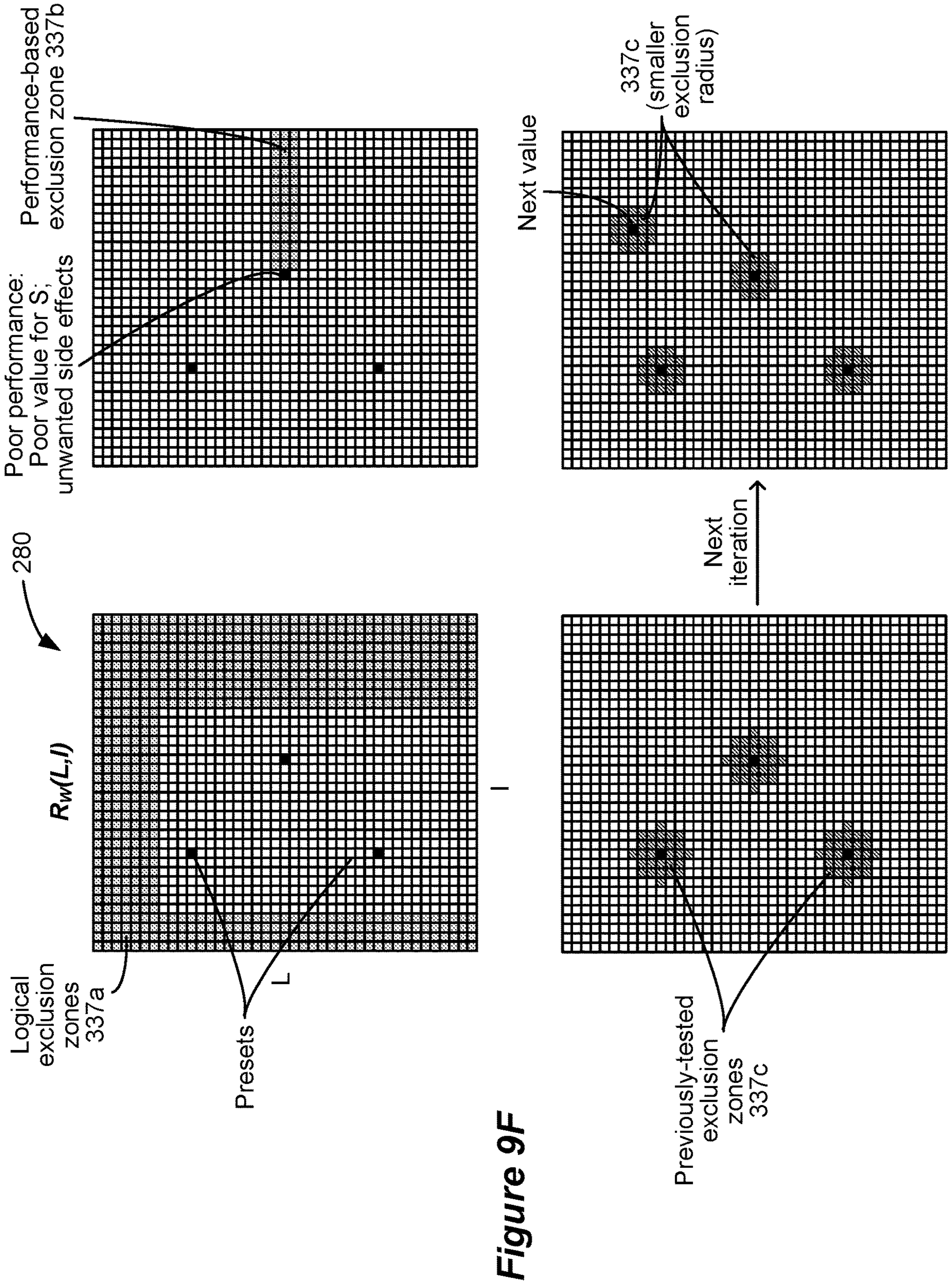

Returning to FIG. 8B, certain $R_W(L,I)$ values can be excluded from the $R_W(L,I)$ data set 280 (337) prior to selecting a next (L,I) value to be tested (338), and this is explained further with reference to FIG. 9F. Specifically, FIG. 9F shows different examples of (L,I) values that can be excluded from data set 280 and the rationale behind their exclusion. Generally speaking, exclusion prevents the algorithm 200 from selecting (L,I) values to be tested that are likely not helpful in determining optimal values Lopt and Iopt1. Exclusion may involve the algorithm 200 applying different exclusion zones that exclude different ranges of (L,I) values. Exclusion zones may be automated via operation of the algorithm 200, or the algorithm 200 may allow the clinician to define exclusions zones. For example, although not shown, the GUI 82 may allow the clinician to define one or more exclusions zones.

For example, the upper left example of the $R_W$(L,I) data set 280 shows different examples of exclusion zones 337*a*, which comprises zones of (L,I) values that are logical to exclude from testing for one reason or another. For example, it may be known that (L,I) values at very low amplitudes I (e.g., less that 0.8 mA) are unlikely to be therapeutically effective for the patient. Therefore, all (L,I) values at such low amplitudes may be logically excluded, as shown by the grey shading at the left. Other logical exclusion zones 337*a* can be defined as well. For example, it may be known from earlier testing in the operating room, or otherwise, that stimulation at particular longitudinal values on the lead 21 are not effective in reducing a particular patient's symptoms, or that stimulation at these longitudinal values creates unwanted side effects. Thus, a zone of L values (e.g., from 6 to 7) may be logically excluded, as shown by the grey shading at the top. Similarly, high amplitude values (e.g., >5 mA) may be logically excluded if they have been observed to be ineffective or side-effect inducing, as shown by the grey shading to the right.

Exclusion zones may also be established based on the results of testing at previous (L,I) values. For example, assume as shown in the upper right of FIG. 9F that poor performance was noted at one or more previously tested (L,I) values (shown here as one of the presets). The poor performance may result from a poor (e.g., high) score (S) determined at this point, and/or because unwanted side effects are observed upon testing at this point. In this instance, it may not be useful to consider other (L,I) values at even higher-amplitude currents, as it might be expected that higher amplitudes will make the performance or side effect worse. Thus, the algorithm 200 automatically, or the clinician manually, may define a performance-based exclusion zone 337*b*. In this example, exclusion zone 337*b* excludes all (L,I) values with higher amplitudes from the poor performance value. Exclusion zone 337*b* also for guard band has excluded some higher-amplitude longitudinal positions around this value as well (at slightly different longitudinal positions from the poor-performing point).

Exclusion zones may 337*c* be also placed around already-tested (L,I) values, as shown at the bottom of FIG. 9F. This excludes the algorithm 200 from selecting a next (L,I) value that is at or close to a previously-tested (L,I) values. This is shown first in FIG. 9F relative to the three preset values. In this example, the algorithm 200 excludes (L,I) values that are within a certain distance (e.g., radius) of the presets, as shown at the bottom left in FIG. 9B. The reason for doing so is that the presets have already been tested and scored, and it is therefore not useful at this point for the algorithm 200 to potentially recommend a next (L,I) value to be tested that is close to the presets. Instead, to encourage the algorithm 200 to explore values more distant from the presets, such close (L,I) values are excluded.

As explained further below, the algorithm 200 will eventually iterate to select a new (L,I) value to test and score, as shown at the bottom right of FIG. 9F. This can result in the addition of new exclusion zones, or the modification of previously-determined exclusion zones to now re-include (L,I) points that were previously excluded. For example, after a next (L,I) value is determined and scored, there are now four (L,I) points that have been tested (including the original three presets). Notice that the exclusion zones 337*c* around each of these points have a reduced radius. This can be useful because while the algorithm 200 generally seeks to select distant next (L,I) values as it iterates, it also does not want to ignore potential (L,I) values of interest that were excluded in earlier iterations simply because these values were close to already tested values. As such, and generally speaking, the exclusion zones may be modified by the algorithm 200 as it iterates, and the shape and size of such zones may change based on step number, i.

To summarize, the algorithm 200 can apply various exclusion rules 337 to exclude one or more less-meaningful values to prevent such values from being selected for testing, thereby increasing the chances that the algorithm will test values that are more meaningful. FIG. 9F shows just some examples of exclusion, but other exclusion rules could be used by the algorithm as well. Note that exclusion of (L,I) points can also occur at different points during the algorithm 200. For example, certain (L,I) values could have been excluded when the data sets 240-270 for the individual factors $R_A$-$R_D$ were determined in steps 332-335.

Although not shown in FIGS. 9A-9E, any of the data sets 240-280 can be displayed to the clinician on the GUI 82. In a useful example, the values of the data at each of the (L,I) values can be mapped to a color, thus allowing the data sets 240-280 to appear as "heat maps" whereby data values and general trends can easily be seen in the data. The ability to view heat maps could be added for example to the GUI shown in FIG. 13, discussed later.

Referring to FIG. 8B, once $R_W$ is determined at each of the (L,I) values, perhaps with some (L,I) values excluded (337), a best $R_W$(L,I) value is selected (338), which determines the next (L,I) value to be tested (330). The best $R_W$(L,I) value can be determined by the algorithm 200 upon reviewing the non-excluded various values for $R_W$ in the data set 280 (FIG. 9E), and selecting the (L,I) value associated with that best (e.g., lowest) value. (Again, and depending on how the factors are processed, a best $R_W$(L,I) value may also have a highest value). In the example of FIG. 9E, the lowest $R_W$(L,I) value is assumed to occur at value (5.0, 6.0), which then comprises the next (L,I) value to be tested. Note that if there is more than one best $R_W$ value in data set 280 (e.g., two or more $R_W$ values having the same lowest value), the algorithm 200 can be programmed with tie-breaking rules to arrive at a single next (L,I) point. For example, the algorithm 200 may prefer to pick a next (L,I) value that has a lowest amplitude, or that is furthest from all previously tested values, etc.

Note that prior data determined upon testing of the patient can be used in place of, or can comprise, a preset value. Further, presets do not necessarily need to be pre-established at set (L,I) points. Instead, the clinician can simply start testing at a particular (L,I) value, record a score, etc. Eventually, when the algorithm 200 has received enough scores at previously-tested (L,I) values, it can begin to automatically determine next values at step 330, and the algorithm can begin to iterate.

Referring again to FIG. 8A, once the next (L,I) value has been determined (330), that value (5.0, 6.0) can be populated into data set 230 as a next step (i=4) and thus as a next point to be applied to the patient (340) and scored by the clinician (345). Again, the electrode configuration algorithm described earlier can determine an electrode configuration suitable to position stimulation at this new longitudinal position. For example, at new (L,I) value (5,6), notice that a ring electrode E3 is located at L=5.0 (FIG. 7), and so that electrode alone will receive all of the cathodic current (100%*–I, or –6.0 mA when 1=6.0 is also considered). Once the electrode configuration is determined, stimulation parameters corresponding to this next (L,I) value are transmitted to the IPG 10 and applied to the patient (340) similarly to what was described earlier for the preset (L,I) values. At least one score (e.g., S=1) is then determined for stimulation occurring at this new (L,I) value (345) and input into the data set 230 as described earlier.

At this point, the algorithm 200 can return to step 320, where a best of the tested values (Lopt, Iopt1) is determined and/or updated. As described earlier, this involves looking at the scores associated with each of the previously-tested points (in steps i=1 to 4 to this point). The best (e.g., lowest) of these scores (0.5) is associated with step i=3, and so (Lopt, Iopt1) remains (3.5, 3.5), which is not updated.

As the algorithm 200 continues, it again determines if one or more stopping criteria have been met (325). Assuming this doesn't occur, the algorithm 200 determines a next (L,I) value to be tested (330) in a next iteration of the algorithm (step i=5). Determining this next (L,I) value essentially occurs as described earlier by determining factors $R_A$-$R_D$ at all points (L,I) (perhaps excepting excluded points). However, notice that there are now more previously-tested points (L,I) to consider (i.e., four, instead of the initial three presets), meaning that the sums in the equations shown in FIGS. 9A-9C involve additional terms (n=4). Again, the factors $R_A$-$R_D$ are weighted to determine $R_W$(L,I), and a next (L,I) value is selected (0, 0.8) for testing using a best value for $R_W$ (see data set 230, FIG. 8A). This next (L,I) value is applied (340) and scored (340) (S=2); (Lopt, Iopt1) is determined and possibly updated (320), etc. The effect of such successive iterations of the algorithm 200 is shown in the data set 230 and the L,I parameter space 210 of FIG. 8A, which shows the (L,I) values that were tested at each iteration (i) of the algorithm 200, and how they logically and efficiently traverse the L,I parameter space 210 as dictated by factors $R_A$-$R_D$ and their weightings. Note that the data shown in FIG. 8A is fictitious and only provided to help illustrate operation of the algorithm 200.

Once a stopping criterium has been met (325), an optimal value of (L,I)—(Lopt, Iopt1)—is determined, which would comprise the (L,I) value determined and updated earlier during step 320. In the illustrated example of the data set 230 in FIG. 8A, it is assumed that the algorithm went through nine iterations (step i=9) before reaching a stopping criterium. Review of the scores at each of the tested (L,I) values yields a best (lowest) score of 0.4, corresponding to Lopt=1.5, Iopt1=5.0 mA (step i=7). Note that there may be more than one best value: for example, two (L,I) values may have the same lowest score. In this case, and although not illustrated, the algorithm 200 may employ tie-breaking rules at step 320 to select a single optimal (L,I) value. For example, from amongst the various potential (L,I) values that are tied, the (L,I) value with the lowest amplitude I, or the lowest energy consumption, may be selected. If more than one score is made at each of the tested values, a point discussed further below with respect to FIG. 14, a value with a best average score, or a best single score, may be selected. It may also be preferred or not preferred to select a (L,I) at a particular longitudinal location. For example, it may be preferred to select as optimal an (L,I) value at a longitudinal value that is proximate to split ring electrodes, as this may allow the algorithm 200 to further optimize the rotational angle of the stimulation, as discussed further below with reference to FIGS. 10-12B. Conversely, it may be preferred to select as optimal an (L,I) value at a longitudinal value that is not proximate to split ring electrodes; this may simplify optimization because rotational angle does not need to be optimized at such longitudinal positions. Other factors may also be used to break a tie between the scores of (L,I) values reflected in data set 230. For example, the optimal (L,I) may be selected as that having the least side effects, or based on other factors of convenience or efficacy.

Note that (Lopt,Iopt1), while optimized for the patient in the manner explained above, is not necessarily the best (L,I) value for the patient: some other (L,I) value not suggested as a next value by the algorithm 200, and therefore not tested, might actually correspond to a best value (e.g., lowest score S). Nevertheless, (Lopt,Iopt1) can still be said to be optimized for the patient, because the algorithm 200 still searches the L,I parameter space 210 efficiently to arrive at a best value of (Lopt, Iopt1) for the patient. In this sense, (Lopt,Iopt1) can be said to be optimized, or comprise a optimal value, for the patient.

At this point, the algorithm 200 determines whether the rotational angle θ at which stimulation will be applied should also be optimized. This depends on the determined position of Lopt in the directional lead 21, and in particular whether Lopt is proximate to split ring electrodes (370). This can require the algorithm 200 to consider the shape and placement of the electrodes on the lead 21. Referring again to FIG. 7, notice that if Lopt >4.0, Lopt is not proximate to any split ring (directional) electrodes on lead 21, and there is therefore no reason to optimize rotational angle. In this circumstance, optimization by the algorithm 200 is complete, with (Lopt, Iopt1) determined as optimal for the patient (380). In other words, an optimal stimulation parameter set has now been determined for the patient: as explained above, from Lopt, the algorithm can determine (using the electrode configuration algorithm) the active electrodes, their polarities, and the percentage of Iopt1 that each active electrode should receive, which along with other non-optimized parameters (e.g., F, PW) comprises the optimized stimulation parameter set.

By contrast, if Lopt <4.0, then split ring electrodes are proximate to Lopt. Note that whether Lopt is proximate to split ring electrodes can depend on the electrode configuration used to set Lopt at that longitudinal position, and whether that electrode configuration involves the use of split ring electrodes. For example, and referring to data set 230, it is seen that split ring electrodes E8-E13 are involved in setting (Lopt, Iopt1)=(1.5, 5.0), which allows the algorithm 200 to conclude that Lopt is proximate to split ring electrodes (370), because at least one split ring electrode is active to fix the position of Lopt.

When the algorithm 200 determines that Lopt is proximate to split ring electrodes (370) as in the depicted example, the algorithm 200 can proceed to determine an optimal rotational angle θopt for the application of stimulation at this longitudinal position Lopt (400), as shown in FIG. 10. Similar to the manner in which longitudinal position was simultaneously optimized (Lopt) with amplitude (Iopt1), the rotational angle of stimulation is also preferably simultaneously optimized (θopt) with amplitude (Iopt2). Because changing the rotational angle θ of the stimulation around the lead 21 changes the tissue receiving the stimulation, it is likely that the amplitude optimized at θopt will be different (Iopt2) from that determined when non-directional stimulation was provided (Iopt1).

Optimizing rotational angle θ in algorithm 200 involves trying different angles θ and amplitudes I at Lopt until θopt and Iopt2 are determined. Optimizing rotational angle θ involves the use of θ,I parameter space 220 (FIG. 7), and for the most part such optimization involves similar steps as were used in the determination of Lopt. Optimization starts with preset values (θ,I) (510) which are chosen to cover a considerable or relevant portion of the possible (θ,I) values in θ,I parameter space 220. In the example shown, four presets are used with (θ,I) values of (0°, 2 mA), (90°, 3.5 mA), (180°, 2 mA), and (270°, 3.5 mA). Again, these are just example presets, and different values could be chosen, and different numbers of presets used. Note that the current amplitude of the presets can also be selected in light of Iopt1 as determined earlier during longitudinal optimization (FIG. 8A). For example, because Iopt1=5.0 mA was determined earlier, current amplitudes equal to or closer to this value may be chosen for the (θ,I) presets. For example, presets of (0°, 4 mA), (90°, 5.5 mA), (180°, 4 mA), and (270°, 5.5 mA) may be used.

Data set 230' keeps track of these values, and also stores (again with help of the electrode configuration algorithm) the electrode configurations needed to provide the stimulation at these different rotational locations, as explained further below. Data set 230' may be a continuation of the data set 230 used during longitudinal optimization (FIG. 8A), or it may comprise a separate data set. Similar to what occurred during longitudinal optimization, the algorithm will determine a next (θ,I) value to test using scores taken at the four presets, as explained further below.

Figure 11A:
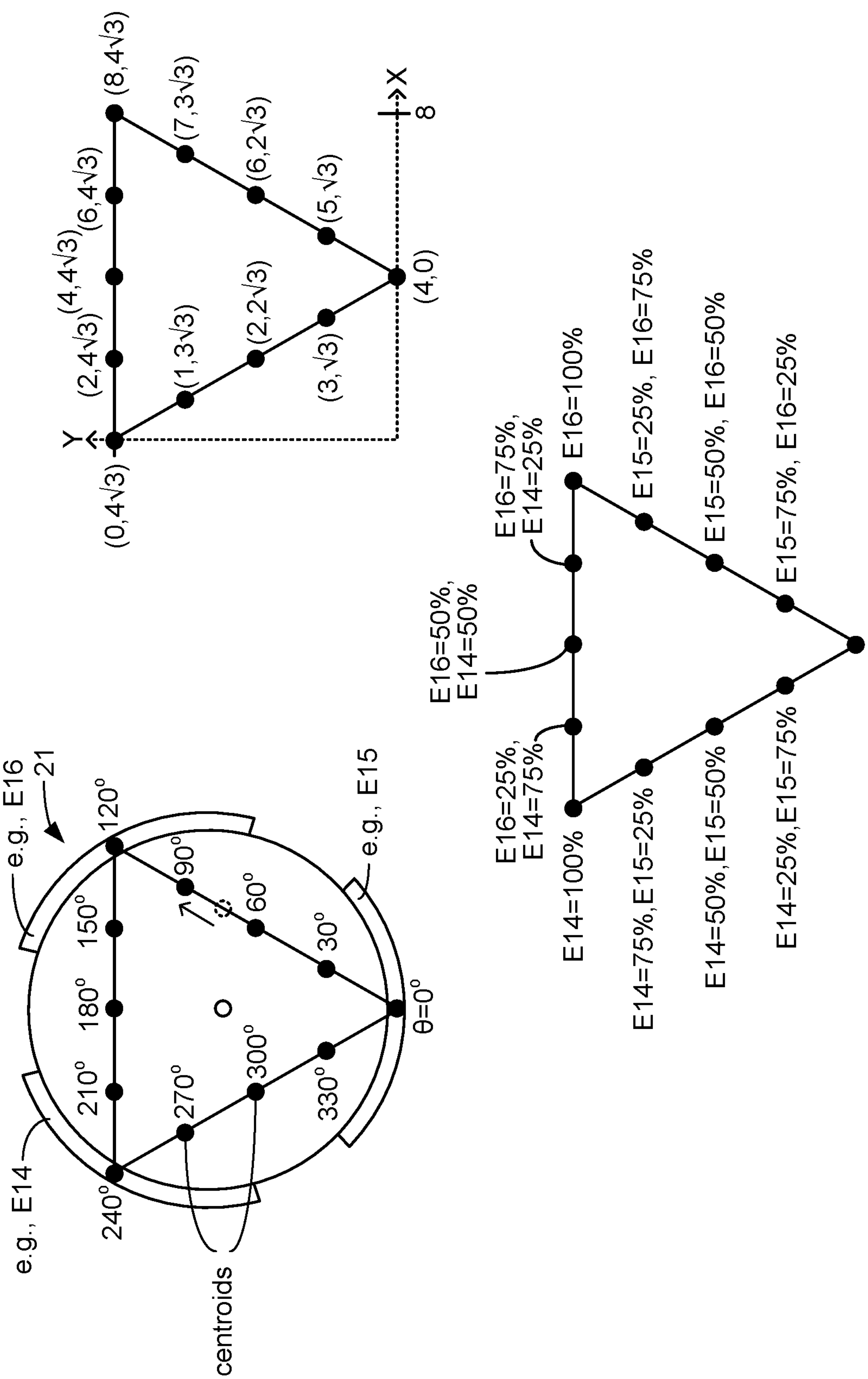
Figures 11B, 11C:
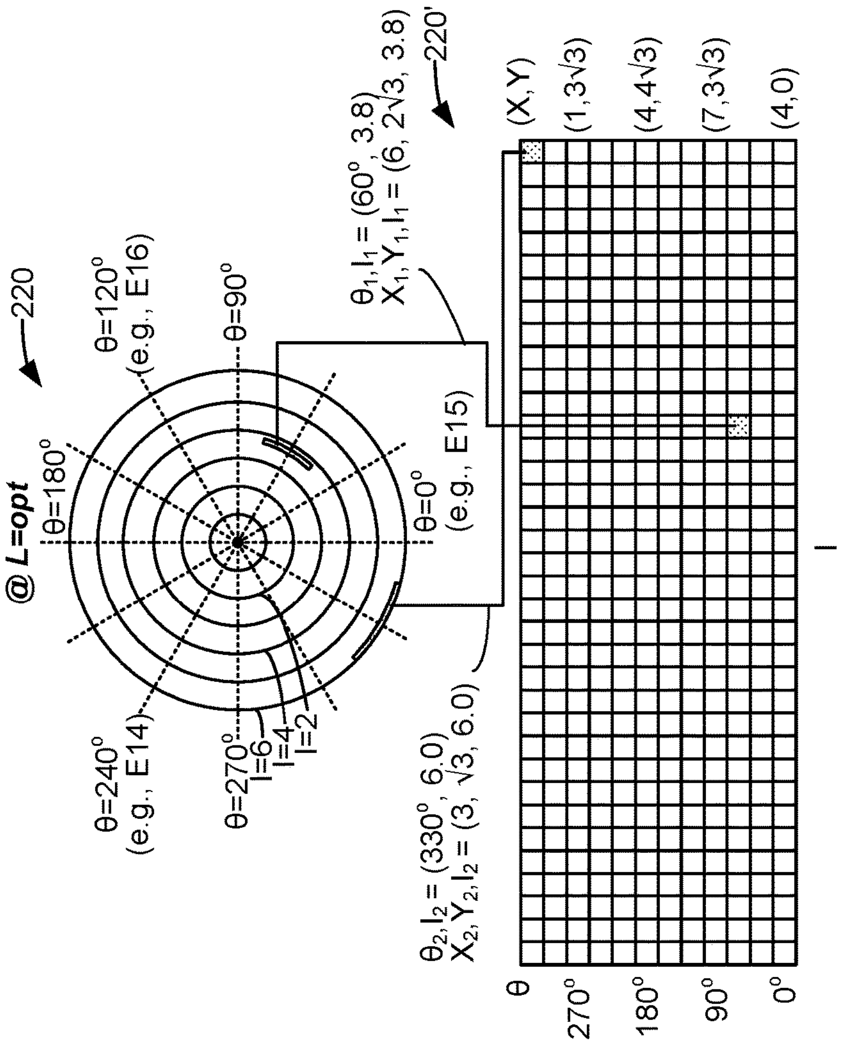

FIGS. 11A-11C are helpful to understanding steps in the algorithm 200 that follow. FIG. 11A shows various representations of the cross section of the directional lead 21 at a longitudinal position having split ring (directional) electrodes. Electrodes E14, E15, and E16 are shown, but split ring electrodes at other longitudinal positions (e.g., E11, E12, E13) would be similarly illustrated. In the example shown, it is assumed that rotational angle θ of the stimulation around the lead 21 is adjustable in 30° increments, although as mentioned earlier a different resolution could be chosen. The upper left drawing in FIG. 11A shows centroids of stimulation (roughly, the centroid of a volume of activation) produced at the various rotational angles θ supported by the system (0°, 30°, 60°, etc.). As shown, these centroids are located on an equilateral triangle, with θ=0° (E15), 120° (E16), and 240° (E14) appearing at the triangle's vertices. For simplicity, other angles are spaced equidistant from each other on the sides of the triangle. Note that this works a slight distortion: for example, the true position of 90° on the triangle relative to the lead 21's center (shown in dotted lines) is different from its actual position (as shown by the arrow). Nevertheless, such distortion is small and is not problematic to operation of the algorithm 200.

The upper right drawing in FIG. 11A shows the position of these centroids in two-dimensional space, i.e., as (X,Y) values. Note as arranged that these centroids range from 0 to 8 in the X direction, and from 0 to $4\sqrt{3}$ (about 6.9) in the Y direction. These X and Y values may represent absolute dimensions (e.g., in mm), but may also comprise generic values indicative of the position of the centroids. As will be seen, the (X,Y) position of these centroids will be useful later during the algorithm 200 to determining distances of potential next (θ,I) values to be tested from those previously tested.

The bottom drawing in FIG. 11A show how the electrode configuration algorithm can fractionalize the current as stimulation is rotated to different centroids, which essentially comprises moving current in 25% increments to and from the relevant electrodes. For example, at 0°, electrode E15 at this location receives 100% of the (cathodic) current –I. Because 30° moves to a centroid in the direction of electrode E16, some of E15's current is shared with E16, amounting to a 75%/25% split in the current, which will cause the centroid to be approximately formed at this angle. At 60°, midway between E15 and E16, the current between E15/E16 is split evenly 50%/50%. At 90°, another 25% percent is moved amounting to a 25%/75% split, until at 120° the current has fully moved to E16 (100%) located at this angle. Centroids at angles from 120° to 240° similarly share current between E16 and E14, and centroids at angles from 240° to 360° (0°) similarly share current between E14 and E15.

FIG. 11B again shows (θ,I) parameter space 220, which is circular and therefore more representative to the user of the system in visualizing the angle θ at which stimulation is applied around the lead 21 during operation of the algorithm 200, as well as the amplitude (I) of the stimulation at that angle. In parameter space 220, amplitude is indicated radially. FIG. 11B also shows a different representation of this parameter space 220'. Parameter space 220' similarly shows angle θ and amplitude I, but additionally shows the coordinates of the centroids (X,Y) used to form stimulation at the appropriate angle θ. Although not depicted as such, note that parameter space 220' can be viewed as three dimensional, as it reflects X, Y (which together designate θ) and I. A couple of different (θ,I) values (i.e., (X,Y,I) values) are shown in FIG. 11B to understand the difference between parameters spaces 220 and 220'.

FIG. 11C shows how distance d' between two data points $(\theta_1,I_1)$ and $(\theta_2,I_2)$ such as the two points shown in FIG. 11B can be computed using parameter space 220', which as will be seen is useful in subsequent steps of the algorithm 200. (Note in the description of rotational optimization that follows that variables are given a prime symbol (e.g., d') to differentiate them from variables used earlier during longitudinal optimization). These points correspond to $(X_1,Y_1,I_1)$ and $(X_2,Y_2,I_2)$, and the distance between them can be expressed as shown in the equation in FIG. 11C. Essentially, this distance d' is Euclidean in nature, and comprises the square root of the sum of the differences (in X, Y, and I) squared. However, because dimensions X and Y can be arbitrary, these squared differences can be weighted. Thus, as shown, the difference in the amplitude I squared is weighed by factor 'a', while the differences in X and Y squared are weighed by factor 'b'. Weights 'a' and 'b' can be selected experimentally, and can vary depending on the difference in relative magnitudes between the amplitude I and the X,Y dimensions. Weights 'a' and 'b' can also be adjusted to provide greater significance to either the amplitude I or the X,Y dimensions in calculating the distance d'. As discussed earlier, distance d' can also be computed in other fashions, using stimulation field modelling (SFM) for example.

Returning again to FIG. 10, the preset (θ,I) values are applied to the patient at Lopt (510). This causes the clinician programmer 70 to transmit stimulation parameter sets indicative of θ and Lopt (as reflected in the electrode configuration) and amplitude I to the IPG 10 so that stimulation can be produced at the prescribed angle and longitudinal position. Because stimulation is provided at Lopt=1.5 in this example, notice during rotational optimization that any of electrodes E8-E13 spanning this longitudinal value may be activated by the electrode configuration algorithm. Further, because Lopt=1.5 is directly between L=2 (E8, E9, E10) and L=1 (E11, E12, and E13), the electrode configuration algorithm will likely always determine that E8 and E11 (at the same angle) should have the same current percentage, as should E9 and E12, and E10 and E13, to place Lopt midway between these electrodes. Thus, at preset (0°, 2), the electrode configuration algorithm would set E9=E12=50%*−I, or −1 mA, to set the cathode pole 99 at zero degrees and at Lopt=1.5. At preset (90°, 3.5), the electrode configuration algorithm would set the currents higher at electrodes E11) and E13 (37.5%*−I, or about −1.3 mA) than E9 and E12 (12.5%*−I, or about −0.4 mA) to position the cathode pole at 90 degrees and at Lopt=1.5, etc.

As each of these presets (θ,I) is sequentially applied to the patient (510), at least one score S' at each of the presets is determined (515) and entered into data set 230' using GUI 82 (FIG. 13). Again, note in the description of rotational optimization that follows that variables are given a prime symbol (e.g., S', R', w') to differentiate them from variables used earlier (FIG. 8A) during longitudinal optimization.

After sequentially applying stimulation according to these presets and determining and recording their scores S' after patient testing, the programming algorithm 200 can determine a best of the (θ,I) values (θopt, Iopt2) tested to this point based on the scores S' provided at each of the previously-tested positions (520). As the algorithm 200 iterates, more (θ,I) values will be tested and scored, and (θopt, Iopt2) can be updated accordingly at this step. At this point, after only testing the presets, (θopt, Iopt2) is determined at step 520 to be (180°, 2) (at step i=3), because this tested value yields the best (e.g., lowest) score (S'=0.3).

Figure 12A:
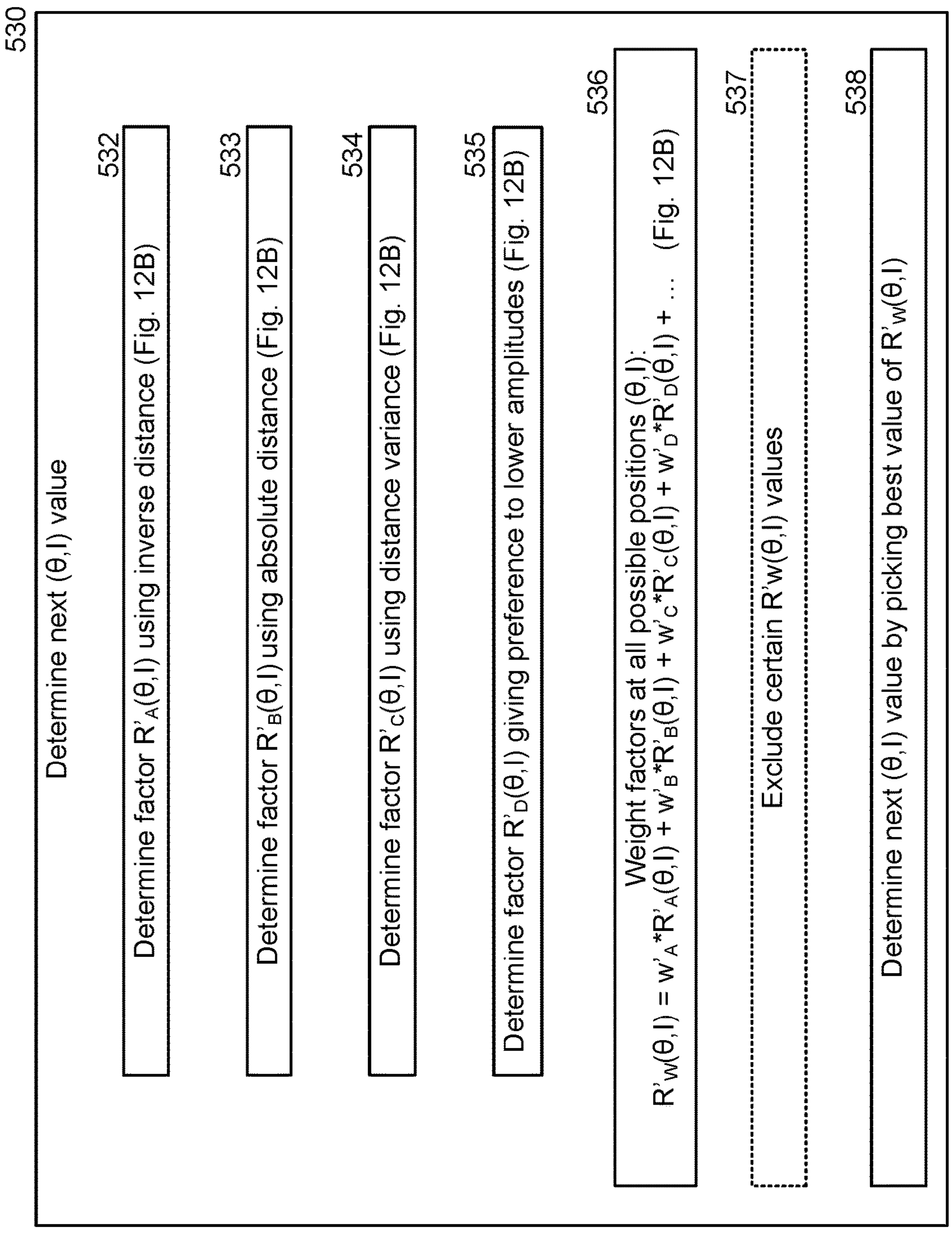
Figure 12B:
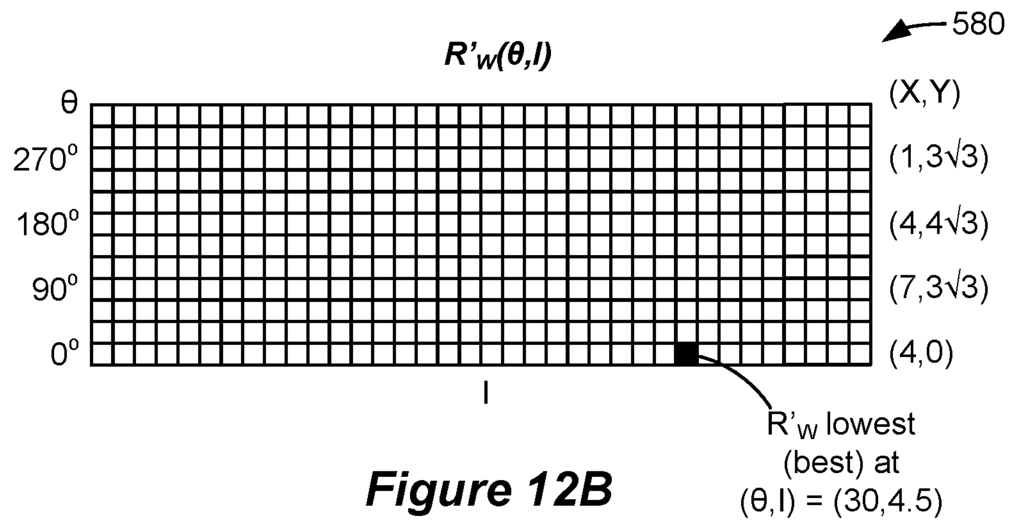

Next, the algorithm 200 determines whether one or more stopping criteria has been met (525), and stopping criteria can be similar to those described earlier for longitudinal optimization. If not, the algorithm 200 continues to determine a next (θ,I) value to be tested (530) in a next iteration of the algorithm (step i=5). Details involved in choosing this next (θ,I) value are shown in FIGS. 12A and 12B. As before, the algorithm 200 computes and considers one or more factors, such as $R'_A$, $R'_B$, $R'_C$, $R'_D$, although again more or fewer factors could be used. Each of these factors is preferably determined at all possible (θ,I) points (532-535) in the θ,I parameter space 220, although certain (θ,I) values can also be excluded (537), as explained earlier.

Step 532 determines factor R'A for all (θ,I) positions using an inverse distance metric, as shown in FIG. 12B. This is similar to what was described earlier, although scores S' and distance d' (FIG. 11C) and power parameter p' are now used in the calculations. Note that the number of entries comprising the $R'_A$ data set again depends on the resolution at which both I (e.g., 0.1 mA) and θ (e.g., in 30° increments) are defined in the system, as well as the extent to which θ,I parameter space 220 is searched.

Step 533 determines a second factor $R'_B$ for all (θ,I) positions using an absolute distance metric, as shown in FIG. 12B. As before, $R'_B$ does not rely on the scores S'i at previously tested points, and instead only relies on distance d' to previously-tested points.

Step 534 determines a third factor $R'_C$ for all (θ,I) positions using a distance variance metric, as shown in FIG. 12B. Again, $R'_C$, like $R'_B$, does not rely on the scores $S'_i$ at previously tested points, but only considers the distances d' to those points.

Step 535 determines a fourth factor $R'_D$ for all (θ,I) positions using a preference for lower amplitudes, as shown in FIG. 12B. As before, $R'_D$ may be preset and not based on the position of or scores at previously tested values. For example, $''_D$ may be higher at (θ,I) points having higher amplitudes (e.g., $R'_D$=4 when I >5 mA) and lower at (θ,I) points having lower amplitudes (e.g., $R'_D$=0 when I<1 mA), which biases the algorithm 200 towards selection of a next (θ,I) to be tested which is at a lower amplitude.

Similar to what was described earlier, algorithm 200 doesn't require the use of all of the factors considered in FIGS. 12A and 12B, and still other factors that aren't shown could be used as well, or computed differently. Further, the various factors determined during longitudinal and rotational optimization can be different, although essentially the same factors are used in both of these optimizations for simple illustration. Data sets corresponding to factors $R'_A$, $R'_B$, $R'_C$, and $R'_D$ are not shown in FIG. 12A or 12B, but would be calculated and stored by the algorithm 200 (e.g., in the clinician programmer 70).

As before, a weighted factor data set $R'_W$ for all (θ,I) positions is determined using the factors $R'_A$, $R'_B$, $R'_C$, and $R'_D$ determined earlier (536). Weights $w'_A$, $w'_C$, and $w'_D$ can be multiplied by their associated factors to yield $R'_W(\theta,I)=w'_A*R'_A(\theta,I)+w'_B*R'_B(\theta,I)+w'_C*R'_C(\theta,I)+w'_D*R'_D(\theta,I)$. As before, the weights w' applied to the factors R' can be varied based on user preferences; the step number i—i.e., how many times the algorithm 200 has iterated to determine a next (θ,I) value; recorded scores S'; or other static or dynamic factors. Further, the factors R'i and or their weights w'i can be normalized or ranked when arriving at $R'_W(\theta,I)$, as explained further above. The resulting values for $R'_W$ at each position (θ,I) is represented by data set 580 as shown in FIG. 12B.

Certain $R'_W(\theta,I)$ values can optionally be excluded from data set 580 (537), such as (θ,I) values that have already been tested and for which a score S' has already been ascertained, or based on other criteria or exclusion zones, as explained earlier with respect to FIG. 9F. Certain (θ,I) values could also have been excluded earlier in the process, such as when the individual factors $R'_A$-$R'_D$ were determined in steps 532-535.

Once $R'_W$ is determined at each of the (θ,I) values (perhaps with some values excluded), a best $R'_W(\theta,I)$ value is selected (538), which determines the next (θ,I) value to be tested (530). In the example shown in FIG. 12B, the best (e.g., lowest) $R'_W(\theta,I)$ value is assumed to occur at value (30°, 4.5), which then comprises the next (θ,I) value to be tested (during step i=5). As before, if there is potentially more than one best value $R'_W$ in data set 580, the algorithm 200 can employ tie-breaking rules.

As was true during longitudinal optimization, any of the data sets $R'_A$, $R'_B$, $R'_C$, $R'_D$, and $R'_W$ can be displayed to the clinician on the GUI 82. In a useful example, the values of the data at each of the (θ,I) values can be mapped to a color, thus allowing the data sets 240-280 to appear as "heat maps" whereby data values and general trends can easily be seen in the data.

As was also true during longitudinal optimization, prior data determined upon testing of the patient can be used in place of, or can comprise, preset values (θ,I). And again, presets do not necessarily need to be pre-established at set (θ,I) points. Instead, the clinician can simply start testing at a particular (θ,I) value, record a score, etc. Eventually, when the algorithm 200 has received enough scores at previously-tested (θ,I) values, it can begin to automatically determine next (θ,I) values to test at step 530, and the algorithm can begin to iterate.

Referring again to FIG. 10, once the next (θ,I) value has been determined (530), that value (30°, 4.5 mA) can be populated into data set 230' as a next step (i=5) and thus as a next point to be tested by the clinician. The electrode configuration algorithm can determine an electrode configuration suitable to position stimulation at this new rotational position and at Lopt: setting E9 and E12 each to 37.5%*–I (about –1.7 mA) and E10 and E13 each to 12.5%*–I (about –0.6 mA) will set stimulation at the desired angle (30°), while also keeping the stimulation longitudinally at Lopt=1.5. Once the electrode configuration is determined, this next (θ,I) value (the stimulation parameter set) is transmitted and applied to the patient (540) similarly to what was described earlier for the preset (θ,I) values. At least one score (S'=2) is then determined for stimulation occurring at this new (θ,I) value and is recorded into the data set 230' (545) using the GUI 82 for example (see FIG. 13).

At this point, the algorithm 200 can return to step 520, wherein a best of the tested values (θopt, Iopt2) is determined and/or updated. (θopt, Iopt2) will remain as (180°, 2.0) (step i=3), because this step shows the best (e.g., lowest) score S' to this point. Assuming a stopping criterium isn't met (525), the algorithm 200 continues iterating and determines a next (θ,I) value to be tested (530) (step i=6), which is applied 540 and for which a score S' is recorded 545, etc. The effect of such successive iterations of the algorithm 200 is shown in the data set 230' and the θ,I parameter space 220 of FIG. 10, which shows the (θ,I) values that are determined and how they logically and efficiently traverse the θ,I parameter space 210 as dictated by factors $R'_A$-$R'_D$ and their weightings. Note that the data shown in FIG. 10 is fictitious and only provided to help illustrate operation of the algorithm 200.

If a stopping criterium has been met (525), no further (θ,I) values are determined or tested, and an optimal value of (θ,I)—(θopt, Iopt2)—is determined, which would comprise the (θ,I) value determined and updated earlier during step 520. In the illustrated example, (θopt, Iopt2) corresponds to the lowest score S' (0.3) when θopt=180° and Iopt2=2.0 mA (step i=3). Notice in this example that (θopt, Iopt2) happens to correspond with one of the presets, but this is coincidental and wouldn't necessarily occur.

At this point, stimulation for the patient has been optimized (450), with Lopt optimized during longitudinal searching, and (if necessary, and depending on Lopt's proximity to split ring electrodes) with θopt and Iopt2 optimized during rotational searching at Lopt. To summarize, algorithm 200 has determined an optimized stimulation parameter set (Lopt, θopt, Iopt2)=(1.5, 180°, 2.0 mA) for the patient. Note that Lopt and θopt, pursuant to the electrode configuration, defines how this amplitude Iopt2=2 mA should be split between the electrodes. As shown in the data set 230' (step i=3), the current Iopt2 should be split equally between electrodes E8, E10, E11, and E13, with each of these electrodes receiving –0.5 mA, which will place the stimulation at the optimal longitudinal (Lopt=1.5) and rotational (θopt=180°) positions relative to the lead 21. Again, other stimulation parameters—such as frequency F and pulse width PW are included as part of the optimized stimulation parameter set, which are assumed to have been optimally determined elsewhere. Like amplitude I, these other stimulation parameters could be optimized using the disclosed technique as well. As was the case with longitudinal optimization, the algorithm 200 may apply tie-breaking rules to select an optimal (θopt, Iopt2) value from between otherwise equally-valued scores S' at step 520. Again, note that (θopt, Iopt2), while optimized for the patient in the manner explained above, is not necessarily the best (θ,I) value for the patient: some other (θ,I) value not suggested as a next value by the algorithm 200, and therefore not tested, might actually correspond to a best value (e.g., lowest score S') for the patient. Nevertheless, (θopt, Iopt2) can still be said to be optimized for the patient, because the algorithm 200 still searches the θ,I parameter space 220 efficiently to arrive at a best value of (θopt, Iopt2) for the patient. In this sense, (θopt, Iopt2) can be said to be optimized, or comprise an optimal value, for the patient.

Also, note in FIG. 6 that even if the algorithm 200 suggests that it is warranted to try and optimize the rotational angle of stimulation (400), such rotational optimization may not necessarily result in better stimulation parameters than were determined during longitudinal optimization (300). For example, all scores received during rotational optimization (S') may be worse (e.g., higher) than the best (e.g., lowest) score (S) determined during longitudinal optimization, which would suggest that directional stimulation is not helpful for the patient. In other words, even if rotational optimization is undertaken, optimal stimulation may still be determined as (Lopt, Iopt1), even if such stimulation parameters are non-directional, and even if such stimulation is located proximate to split ring electrodes.

FIG. 13 shows the GUI 82 that may be used to implement the programming algorithm 200, and displays information that may be useful to the clinician as the algorithm 200 operates. GUI 82 may include a user-selectable option allowing the clinician to "run programming algorithm 200." Upon selection of this option, a longitudinal optimization section 550 may be displayed, including aspects of data set 230 and parameter space 210 that are useful in understanding how the algorithm 200 is progressing during longitudinal optimization. As noted earlier, data set 230 displays preset and next-determined values (L,I), and allows the clinician to input the score (S) at each. Once a stopping criterium is met, the GUI 82 can display the determined values for Lopt and Iopt1, along with other useful information such as its (best) score S, and perhaps even the electrode configuration and/or stimulation parameters that places the stimulation at that position.

If the algorithm 200 determines based on Lopt that rotational optimization is recommended (see FIG. 8A, 370), this fact can be displayed to the clinician as a selectable option (552) to allow such rotational optimization to commence. Otherwise, the GUI 82 can display that rotational optimization is not necessary, and that optimization is (Lopt, Iopt1) is complete (not shown). If rotational optimization is undertaken, the GUI 82 can display a rotational optimization section 555, including aspects of data set 230' and parameter space 220 that are useful in understanding how the algorithm 200 is progressing during rotational optimization. As before, data set 230' displays preset and next-determined values (θ,I), and allows the clinician to input the scores (S') at each. Once a stopping criterium is met, the GUI 82 can display the determined values for Lopt, θopt, Iopt2, along with other useful information such as its (best) score S', and perhaps even the electrode configuration and/or stimulation parameters that places the stimulation at that position. Although not shown, the GUI 82 of FIG. 13 may also include a picture of the lead for which stimulation is being optimized, along with the location of the cathode pole 99 that is formed by the optimized stimulation, similar to what was shown in FIG. 5A.

Notice that programming algorithm 200 addresses problems of determining optimal stimulation for DBS patients. As mentioned earlier, in a typical DBS system there are many combinations of I, L, and θ that that can be tested and scored when determining optimal stimulation parameters, and testing all such combinations is burdensome and impractical during a programming session. Use of the programming algorithm 200 efficiently and automatically selects next values to test, and automatically decides when enough values have been tested. As such, much of the guess work in selecting optimal stimulation parameters is removed, and optimal stimulation parameters can be arrived at efficiently and in a reasonable period of time, such as during a typical programming session.

Many modifications can be made to the programming algorithm 200 as described up to this point. Use of the algorithm 200 has been described as particularly useful when used to determine stimulation parameters for a patient having a directional lead (e.g., 19 or 21) with split ring electrodes at least some longitudinal positions on the lead. With such a lead, both longitudinal optimization and rotational optimization can be useful. However, algorithm 200 may also be used in part to provide only longitudinal optimization or only rotational optimization. For example, only longitudinal optimization aspects of the technique (e.g., FIGS. 8A to 9E) may be used to determine Lopt in a directional lead 21; rotational optimization may not be necessary, or if necessary could occur via other means. Likewise, only rotational optimization aspects of the technique (e.g., FIGS. 10 to 12B) may be used to determine θopt at a particularly longitudinal position along a directional lead, which may be particularly useful if the longitudinal position of the stimulation along the lead (e.g., Lopt) is already known or has been determined by other means. Even if Lopt is not known, the algorithm 200 may still apply only rotational optimization at a given longitudinal position L of the clinician's choosing.

Furthermore, while the algorithm 200 has been described sequentially as comprising longitudinal optimization followed by rotational optimization, the order could be reversed. Still further, longitudinal optimization and rotational optimization can occur more than once. For example, longitudinal optimization may occur to determine Lopt1; followed by rotational optimization to determine θopt1 at Lopt1; followed by further longitudinal optimization to perhaps further optimize Lopt2 at θopt1; followed by further rotational optimization to perhaps further optimize θopt2 at Lopt2; etc.

The algorithm 200 may also be used with non-directional leads (e.g., 18, FIG. 1B) having only circumferential ring electrodes, or with paddle leads. See, e.g., U.S. Pat. No. 10,149,979 (describing paddle leads in a Spinal Cord Stimulation (SC S) system). In these circumstances, only longitudinal optimization aspects of the technique may be necessary.

FIG. 14 shows another modification to programming algorithm 200. In this modification, the clinician can enter a plurality of scores S at each tested stimulation parameter at each iteration of the algorithm. FIG. 14 illustrates this only with respect to longitudinal optimization for simplicity, although this could also be applied to rotational optimization (FIGS. 10-12B). As shown, three scores $S_1$, $S_2$, and $S_3$ are determined at each step, although two or more than three could also be considered. For example, $S_1$ can comprise a bradykinesia score; $S_2$ a rigidity score; $S_3$ may score the severity of an undesired side effect or may comprise a generic side effect ranking. Again, these are just examples; other subjectively determined or objectively measured patient outcomes can be scored as noted earlier. See U.S. Patent Application Publication 2021/0196956 (discussing determination of a plurality of scores for a given stimulation parameter set in a DBS application).

In Example 1, the scores $S_1$, $S_2$, and $S_3$ are weighted (per weights e, f, and g) to arrive at $S_T$, which is then used to assist in selecting a next value to be tested. Note that such weighting can comprise averaging the scores $S_1$, $S_2$, and $S_3$. Once $S_T$ values are determined at previously tested locations, the algorithm 200 can proceed as before to determine a next value to be tested. Thus, and in light of scores $S_T$ determined at earlier steps, data sets $R_{TA}$(L,I), $R_{TB}$(L,I), $R_{TC}$(L,I), and $R_{TD}$(L,I) can be determined (see FIGS. 9A-9D), and these can be weighted to determined a weighted data set $R_W$(L,I) (see FIG. 9E), which can be used to choose the next value ((L,I) in this case) to be tested by determining a best (e.g., lowest) value in $R_W$(L,I).

Example 2 also involves determining a weighted data set $R_W$(L,I) that can be used to select next values to be tested, although this doesn't use $S_T$ to do so. Instead, in this example, each of the individual scores $S_1$, $S_2$, and $S_3$ are processed separately to arrive at a weighted data set associated with that score ($R_{1W}$(L,I), $R_{2W}$(L,I), and $R_{3W}$(L,I)), and then these weighted data sets are weighted again (per e, f, and g) to arrive at data set $R_W$. This example is beneficial because the weights used to form the $R_{iW}$(L,I) data set for each score $S_i$ can be set differently if desired (e.g., $w_{iA}$, $w_{iB}$, $w_{iC}$, $w_{iD}$). Again, use of multiple scores S' can also be used during rotational optimization to determine a next (θ,I) value to be tested.

Regardless of how $R_W$(L,I) is determined and used to select next points to be tested, the algorithm 200 can use any of the scores to ultimately select optimal stimulation parameters (in this case, Lopt and Iopt1). For example, once data set 230 is complete and all values have been tested, $S_T$ can be assessed to determine Lopt and Iopt1 in this example, which may make sense as $S_T$ comprises a general averaging of the individual scores $S_1$, $S_2$, and $S_3$. If $S_T$ is used in this manner, the algorithm 200 would determine that Lopt=3.2, and Iopt1=1.2 mA (step i=8), because this step corresponds to the best (lowest) value for $S_T$ (0.3) in data set 230. Alternatively, the algorithm 200 could use any of the individual scores in data set 230 to determine optimal parameters. Assume for example that $S_1$ scores a particularly important symptom such as bradykinesia. The algorithm 200 may thus use this score $S_1$ to determine the optimal parameters. If $S_1$ is used in this manner, the algorithm 200 would determine that Lopt=1.5, and Iopt1=5.0 mA (step i=7), because this step corresponds to the best (lowest) value for $S_1$ (0.4) in data set 230. $S_T$ by contrast may be used only to assist in selecting the next values to be tested, or may not be used at all. Still alternatively, algorithm 200 could assess all scores $S_1$, $S_2$, $S_3$, and $S_T$, and use the best (lowest) value of all of these to select the optimal parameters.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for optimizing stimulation for a patient having an implantable stimulator device, wherein the stimulation device comprises a lead with a plurality of electrodes for providing stimulation in accordance with stimulation parameters, the method comprising:

providing stimulation during first testing at a plurality of different first combinations of longitudinal positions and amplitudes along the lead;

determining for the patient through the first testing an optimized longitudinal position along an axis of the lead and a first optimized amplitude for stimulation, wherein the optimized longitudinal position and the first optimized amplitude comprise first stimulation parameters, wherein the optimized longitudinal position is defined by a first of the electrodes;

determining whether the optimized longitudinal position is proximate to a set of directional electrodes on the lead by determining whether the first electrodes comprise one or more directional electrodes in a set, wherein the set of directional electrodes span around the axis of the lead at different rotational positions;

if it is determined that the optimized longitudinal position is not proximate to the set of directional electrodes on the lead because the first electrodes do not comprise one or more of the directional electrodes, providing stimulation to the patient using determining that the first stimulation parameters; and if it is determined that the optimized longitudinal position is proximate to the set of directional electrodes on the lead because the first electrodes do comprise one or more of the directional electrodes, providing stimulation during second testing at a plurality of different second combinations of rotational positions and amplitudes at the optimized longitudinal position using at least the set of directional electrodes, determining for the patient through the second testing an optimized rotational position and a second optimized amplitude for stimulation at the optimized longitudinal position, wherein the optimized longitudinal position, the optimized rotational position, and the second optimized amplitude comprise second stimulation parameters, and providing stimulation to the patient using the second stimulation parameters.

2. The method of claim 1, wherein determining the optimized longitudinal position and the first optimized amplitude comprises:

receiving at least one first score at each of the first combinations; and determining the optimized longitudinal position and the first optimized amplitude using at least the at least one first score at each of the first combinations.

3. The method of claim 2, wherein at least some of the different first combinations are determined through an iterative process.

4. The method of claim 3, wherein the iterative process provides stimulation at initial first combinations, and automatically determines a next first combination for providing stimulation using at least the at least one first score at each of the initial first combinations.

5. The method of claim 4, further comprising determining at least one first factor, wherein the at least one first factor is determined at a plurality of first possible combinations of longitudinal positions and amplitudes, wherein the at least one first factor at each of the plurality of first possible combinations is determined:

using a distance between each of the plurality of first possible combinations and each of the initial first combinations, and/or using at least the at least one first score at each of the initial first combinations.

6. The method of claim 5, wherein there are a plurality of first factors, and wherein the first factors are used to determine weighted first factors at the first possible combinations.

7. The method of claim 6, wherein the next first combination is determined at a best value of the weighted first factors.

8. The method of claim 4, wherein the iterative process repeats to determine subsequent next first combinations using at least the at least one first score at each of the initial first combinations and the at least one first score at the next first combination.

9. The method of claim 1, wherein the at least one first score at each of the first combinations is indicative of a patient symptom, a patient response, or a side effect to the provided stimulation.

10. The method of claim 1, wherein determining the optimized rotational position and the second optimized amplitude comprises:

receiving at least one second score at each of the second combinations; and determining the optimized rotational position and the second optimized amplitude for the patient using at least the at least one second score at each of the second combinations.

11. The method of claim 10, wherein at least some of the different second combinations are determined through an iterative process.

12. The method of claim 11, wherein the iterative process provides stimulation at initial second combinations, and automatically determines a next second combination for providing stimulation using at least the at least one second score at each of the initial second combinations.

13. The method of claim 12, further comprising determining at least one second factor, wherein the at least one second factor is determined at a plurality of second possible combinations of rotational positions and amplitudes, wherein the at least one second factor at each of the plurality of second possible combinations is determined:

using a distance between each of the plurality of second possible combinations and each of the initial second combinations, and/or using at least the at least one second score at each of the initial second combinations.

14. The method of claim 13, wherein there are a plurality of second factors, and wherein the second factors are used to determine weighted second factors at the second possible combinations, wherein the next second combination is determined at a best value of the weighted second factors.

15. The method of claim 12, wherein the iterative process repeats to determine subsequent next second combinations using at least the at least one second score at each of the initial second combinations and the at least one second score at the next second combination.

16. A system, comprising:

an implantable stimulator device implantable in a patient, wherein the stimulation device comprises a lead with a plurality of electrodes for providing stimulation in accordance with stimulation parameters; and an external device programmed with an algorithm and configured to communicate with the implantable stimulator device, wherein the algorithm is configured to provide stimulation during first testing at a plurality of different first combinations of longitudinal positions and amplitudes along the lead;

determine for the patient through the first testing an optimized longitudinal position along an axis of the lead and a first optimized amplitude for stimulation, wherein the optimized longitudinal position and the first optimized amplitude comprise first stimulation parameters, wherein the optimized longitudinal position is defined by a first of the electrodes;

determine whether the optimized longitudinal position is proximate to a set of directional electrodes on the lead by determining whether the first electrodes comprise one or more directional electrodes in a set, wherein the set of directional electrodes span around the axis of the lead at different rotational positions;

if it is determined that the optimized longitudinal position is not proximate to the set of directional electrodes on the lead because the first electrodes do not comprise one or more of the directional electrodes, provide stimulation to the patient using the first stimulation parameters; and if it is determined that the optimized longitudinal position is proximate to the set of directional electrodes on the lead because the first electrodes do comprise one or more of the directional electrodes, providing stimulation during second testing at a plurality of different second combinations of rotational positions and amplitudes at the optimized longitudinal position using at least the set of directional electrodes, determine for the patient through the second testing an optimized rotational position and a second optimized amplitude for stimulation at the optimized longitudinal position, wherein the optimized longitudinal position, the optimized rotational position, and the second optimized amplitude comprise second stimulation parameters, and provide stimulation to the patient using the second stimulation parameters.

* * * * *